(12) United States Patent
Shaoulian et al.

(10) Patent No.: US 7,357,815 B2
(45) Date of Patent: Apr. 15, 2008

(54) DYNAMICALLY ADJUSTABLE IMPLANTS AND METHODS FOR RESHAPING TISSUE

(75) Inventors: Emanuel Shaoulian, Newport Beach, CA (US); Shahram Moaddeb, Irvine, CA (US); Samuel M. Shaolian, Newport Beach, CA (US)

(73) Assignee: Micardia Corporation, Irvine, CA (US)

( * ) Notice: Subject to any disclaimer, the term of this patent is extended or adjusted under 35 U.S.C. 154(b) by 300 days.

(21) Appl. No.: 11/123,874

(22) Filed: May 6, 2005

(65) Prior Publication Data

US 2006/0241747 A1    Oct. 26, 2006

Related U.S. Application Data

(60) Provisional application No. 60/673,419, filed on Apr. 21, 2005.

(51) Int. Cl.
A61F 2/06    (2006.01)

(52) U.S. Cl. .................................. 623/2.36; 623/2.37

(58) Field of Classification Search ....... 623/2.36–2.37
See application file for complete search history.

(56) References Cited

U.S. PATENT DOCUMENTS

| | | | |
|---|---|---|---|
| 4,233,690 A | 11/1980 | Akins | |
| 4,507,115 A | 3/1985 | Kambara et al. | |
| 4,556,050 A | 12/1985 | Hdogson et al. | |
| 4,665,906 A | 5/1987 | Jervis | |
| 4,805,618 A | 2/1989 | Ueda et al. | |
| 5,171,252 A | 12/1992 | Friedland | |
| 5,350,413 A | 9/1994 | Miller | |
| 5,415,623 A | 5/1995 | Cherubini | |
| 5,850,837 A | 12/1998 | Shiroyama et al. | |
| 5,979,456 A | 11/1999 | Magovern | |
| 6,273,908 B1 | 8/2001 | Ndondo-Lay | |
| 6,397,109 B1 | 5/2002 | Cammilli et al. | |

(Continued)

FOREIGN PATENT DOCUMENTS

WO    WO/96/34211    10/1996

OTHER PUBLICATIONS

Lendlein and Langer, "Sciencexpress: Biodegradable, elastic shape memory polymers for potential biomedical applications," Apr. 25, 2002.

(Continued)

*Primary Examiner*—Suzette Gherbi
(74) *Attorney, Agent, or Firm*—James W. Hill; McDermott Will & Emery LLP

(57) ABSTRACT

Tissue shaping methods and devices are provided. The devices can be adjusted within the body of a patient in a less invasive or non-invasive manner, such as by applying energy percutaneously or external to the patient's body. In one example, the device is positioned within the coronary sinus of the patient so as to effect changes in at least one dimension of the mitral valve annulus. The device may also advantageously include a shape memory material that is responsive to changes in temperature and/or exposure to a magnetic field. In one example, the shape memory material is responsive to energy, such as electromagnetic or acoustic energy, applied from an energy source located outside the coronary sinus. A material having enhanced absorption characteristics with respect to the desired heating energy may also be used to facilitate heating and adjustment of the tissue shaping device.

22 Claims, 16 Drawing Sheets

U.S. PATENT DOCUMENTS

| | | |
|---|---|---|
| 6,569,198 B1 | 5/2003 | Wilson et al. |
| 6,656,221 B2 | 12/2003 | Taylor et al. |
| 6,676,702 B2 | 1/2004 | Mathis |
| 6,740,094 B2 | 5/2004 | Maitland et al. |
| 6,764,510 B2 | 7/2004 | Vidlund et al. |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,890,353 B2 | 5/2005 | Cohn et al. |
| 6,997,951 B2 | 2/2006 | Solem et al. |
| 7,101,395 B2 * | 9/2006 | Tremulis et al. ............ 623/2.11 |
| 7,144,363 B2 * | 12/2006 | Pai et al. ...................... 600/16 |
| 2002/0087173 A1 | 7/2002 | Alferness et al. |
| 2002/0151961 A1 | 10/2002 | Lashinski et al. |
| 2002/0183837 A1 | 12/2002 | Streeter et al. |
| 2002/0183838 A1 | 12/2002 | Liddicoat et al. |
| 2003/0078654 A1 | 4/2003 | Taylor et al. |
| 2003/0083538 A1 | 5/2003 | Adams et al. |
| 2003/0130730 A1 | 7/2003 | Cohn et al. |
| 2003/0135267 A1 | 7/2003 | Solem et al. |
| 2003/0144697 A1 | 7/2003 | Mathis et al. |
| 2003/0171806 A1 | 9/2003 | Mathis et al. |
| 2004/0019377 A1 | 1/2004 | Taylor et al. |
| 2004/0073302 A1 | 4/2004 | Rourke et al. |
| 2004/0093017 A1 | 5/2004 | Chanduszki |
| 2004/0098116 A1 | 5/2004 | Callas et al. |
| 2004/0102839 A1 | 5/2004 | Cohn et al. |
| 2004/0102841 A1 | 5/2004 | Langberg et al. |
| 2004/0138744 A1 | 7/2004 | Lashinski et al. |
| 2004/0153146 A1 | 8/2004 | Lashinski et al. |
| 2004/0153147 A1 | 8/2004 | Mathis |
| 2004/0220657 A1 | 11/2004 | Nieminen et al. |
| 2004/0243227 A1 | 12/2004 | Starksen et al. |
| 2004/0250820 A1 | 12/2004 | Forsell |
| 2005/0027351 A1 | 2/2005 | Reuter et al. |
| 2005/0038506 A1 | 2/2005 | Webler et al. |
| 2005/0043792 A1 | 2/2005 | Solem et al. |
| 2005/0055087 A1 | 3/2005 | Starksen |
| 2005/0055089 A1 | 3/2005 | Macoviak et al. |
| 2005/0060030 A1 | 3/2005 | Lashinski et al. |
| 2005/0070998 A1 | 3/2005 | Rourke et al. |
| 2005/0080483 A1 | 4/2005 | Solem et al. |
| 2005/0119733 A1 | 6/2005 | Williams et al. |
| 2006/0015002 A1 * | 1/2006 | Moaddeb et al. ............. 600/37 |
| 2007/0010878 A1 * | 1/2007 | Rafiee et al. ............... 623/2.36 |

OTHER PUBLICATIONS

Ryklina et al., Two-way shape memory effect inducing in NiTi Alloy and its Application to a Device for Clipping Blood Vessels.

* cited by examiner

DYNAMICALLY ADJUSTABLE IMPLANTS AND METHODS FOR RESHAPING TISSUE

RELATED APPLICATION

This application claims the benefit of priority under 35 U.S.C. § 119(e) of U.S. Provisional Application No. 60/673, 419, filed on Apr. 21, 2005, and entitled "DYNAMICALLY ADJUSTABLE IMPLANTS AND METHODS FOR RESHAPING TISSUE," the entirety of which is hereby incorporated herein by reference.

BACKGROUND OF THE INVENTION

1. Field of the Invention

The present invention generally relates to implants and methods to reshape tissue and, more specifically, to dynamically reshape and resize the mitral valve annulus of a heart.

2. Description of the Related Art

In recent years, hundreds of thousands of individuals have undergone mitral valve replacement or repair. The mitral valve is a portion of the heart that is located between the chambers of the left atrium and the left ventricle. When the left ventricle contracts to pump blood throughout the body, the mitral valve closes to prevent the blood from being pumped back into the left atrium. In some individuals, whether due to genetic malformation, disease or injury, the mitral valve fails to close properly, causing a condition known as mitral regurgitation, whereby blood is pumped into the atrium upon each contraction of the heart muscle.

Mitral regurgitation is a serious, often rapidly deteriorating, condition that reduces circulatory efficiency. Oftentimes, mitral regurgitation is caused by geometric changes of the left ventricle, papillary muscles and mitral annulus. For example, certain diseases of the heart valves can result in dilation of the heart and one or more heart valves. When a heart valve annulus dilates, the valve leaflet geometry deforms and causes ineffective closure of the valve leaflets. The ineffective closure of the valve, or incomplete coaptation of the valve leaflets, can cause regurgitation of the blood, accumulation of blood in the heart and other problems.

Two of the more common techniques for restoring the function of a damaged mitral valve are valve replacement surgery and annuloplasty. In valve replacement surgery, the damaged leaflets are surgically excised, and the mitral valve annulus is sculpted to receive a replacement mechanical valve. In annuloplasty, the effective size of the valve annulus is contracted by attaching a prosthetic annuloplasty repair segment or ring to an interior wall of the heart around the valve annulus. The annuloplasty ring reinforces the functional changes that occur during the cardiac cycle to improve coaptation and valve integrity. Thus, annuloplasty rings help reduce reverse flow or regurgitation while permitting good hemodynamics during forward flow.

Each of these procedures, however, is highly invasive because access to the heart is obtained through an opening in the patient's chest, with the heart being bypassed to a heart-lung machine throughout the procedure. Most patients with mitral valve regurgitation, however, are often relatively frail, thereby increasing the risks associated with such an operation.

In response to the foregoing drawbacks, less invasive approaches have been proposed for aiding the closure of the mitral valve. These procedures involve the percutaneous placement of a manually-adjustable support structure in the coronary sinus close to the posterior leaflet of the mitral valve. The support structure is designed to push the vessel and surrounding tissue toward the anterior wall of the valve to aid its closure and to improve leaflet coaptation. This procedure, however, has several drawbacks. For example, the support structure does not allow for non-invasive alteration or adjustment and is oftentimes permanently implanted within the patient. Furthermore, a surgeon is unable to reduce the force of the support structure to reduce risk of artery pinching and is further unable to readjust the shape and size of the support structure post-implant or during the implantation.

SUMMARY OF THE INVENTION

In view of the foregoing, conventional systems and methods for treating valvular insufficiency do not provide for a less invasive approach that reduces strain on the patient. A need, therefore, remains for devices and methods that allow for non-invasive adjustment of an implant usable to treat valvular insufficiency and, in particular, mitral valvular insufficiency. Furthermore, a need exists for an implant that may be dynamically adjusted post-implantation through a non-invasive means.

In one embodiment, an implant is disclosed for applying pressure to a mitral valve of a heart of a patient. The implant includes a body having a proximal end, a distal end and a length extending therebetween, the body being further configured to fit in a coronary sinus of the heart. The body further comprises at least one shape memory portion consisting essentially of at least one shape memory material, the at least one shape memory portion extending at least half the length of the body. Furthermore, the at least one shape memory portion, when activated by an energy source located outside the coronary sinus and unattached to the implant, is transformable from a first configuration to a second configuration while the body is in the coronary sinus.

In another embodiment, a method is disclosed for treating mitral valve disease. The method includes providing an implant comprising a body having a proximal end, a distal end and a length extending therebetween, wherein the body comprises at least one shape memory portion consisting essentially of at least one shape memory material, the at least one shape memory portion extending at least half the length of the body. The method also includes positioning the implant in a coronary sinus of the heart. In a further embodiment, the method further includes activating the implant with an energy source to cause the at least one shape memory portion to transform from a first configuration to a second configuration while the implant is in the coronary sinus.

In another embodiment, a device is disclosed for reshaping or reforming body tissue. The device includes elongate, flexible means for changing a dimension of a mitral valve annulus, the elongate, flexible means having a first end, a second end and a length extending therebetween, wherein the elongate, flexible means is configured to fit within a coronary sinus of a heart. The elongate, flexible means further comprises means for receiving energy from a source located outside the coronary sinus and unattached to the device, the means for receiving consisting essentially of at least one shape memory material and extending at least half the length of the body, the means for receiving capable of transforming the elongate, flexible means from a first configuration to a second configuration while the device is in the coronary sinus.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

DETAILED DESCRIPTION OF THE PREFERRED EMBODIMENTS

Figure 1:
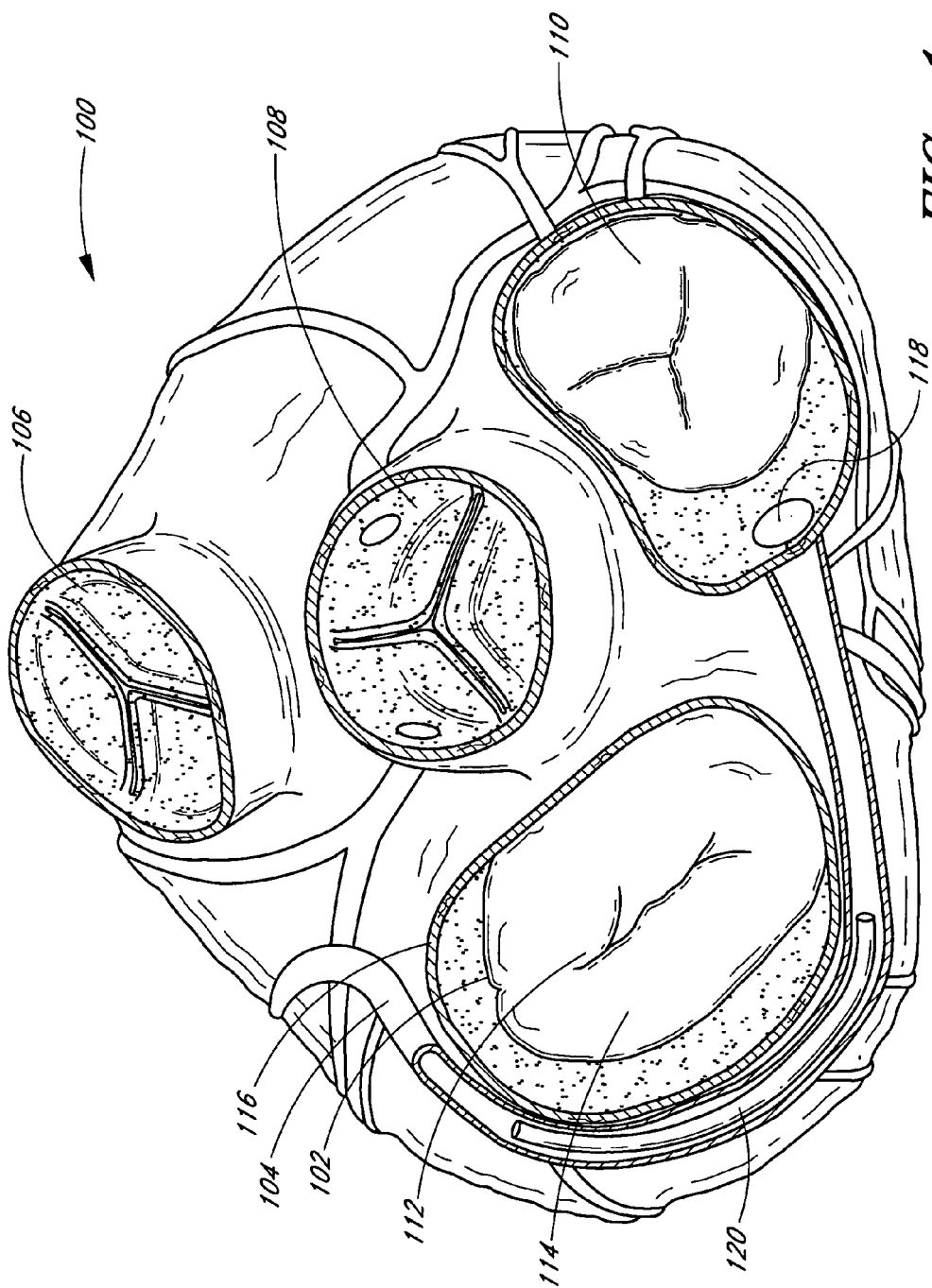
FIG. 1 illustrates a schematic view of a tissue shaping device positioned within a coronary sinus of a heart according to certain embodiments of the invention.

The present invention involves devices and methods to reshape tissue, such as by reinforcing dysfunctional heart valves and other body tissue through a dynamically adjustable implant. Although embodiments of the invention disclosed herein are described with reference to the reshaping and/or resizing of a mitral valve of a human heart, embodiments of the invention may also be used with a wide variety of other valves, vessels, and/or tissue that require reshaping or reforming. For example, certain embodiments may be used to change at least one dimension of the tricuspid valve, the pulmonary valve, or the aortic valve. In yet other embodiments, the tissue shaping device 120 may be used to reshape or reform left or right ventricles, gastric system tissue and/or organs (e.g., stomach), or the like.

In certain embodiments, a dynamically adjustable tissue shaping device is used to reshape and resize the mitral valve annulus via implanting the device within the coronary sinus of a patient. In particular, the tissue shaping device is used to dynamically change at least one dimension of the mitral valve annulus to improve leaflet coaptation and to reduce regurgitation. After implantation, the shape of the tissue shaping device can be further adjusted to compensate for changes in the size of the heart. For example, the tissue shaping device may be implanted in a child whose heart grows as the child gets older. Thus, the shape of the tissue shaping device may need to be modified to allow for expansion. As another example, the size of an enlarged heart may start to return to its normal size after implantation. Thus, the shape of the tissue shaping device may need to be modified to continue to reinforce the mitral valve annulus.

In certain embodiments, the tissue shaping device comprises a shape memory material that is responsive to changes in temperature and/or exposure to a magnetic field. Shape memory is the ability of a material to regain or return to a particular shape after deformation. Shape memory materials include, for example, polymers, metals, metal alloys and ferromagnetic alloys. In certain embodiments, the tissue shaping device is adjusted in vivo by applying an energy source to activate the shape memory material and cause it to change to a memorized or prior shape. The energy source may include, for example, radio frequency (RF) energy, x-ray energy, microwave energy, acoustic or ultrasonic energy such as high intensity focused ultrasound (HIFU) energy, light energy, electric field energy, magnetic field energy, combinations of the same, or the like. For example, one embodiment of electromagnetic radiation may include infrared energy having a wavelength in a range between approximately 750 nanometers and approximately 1600 nanometers. This type of infrared radiation may be produced by a solid state diode laser.

In certain embodiments, the tissue shaping device further includes an energy absorbing material to increase heating efficiency and substantially localize heating in a select area of the shape memory material. Thus, damage to the surrounding tissue is reduced or minimized. Energy absorbing materials for light or laser activation energy may include nanoshells, nanospheres and the like, particularly where infrared laser energy is used to energize the material. Such nanoparticles may be made from a dielectric, such as silica, coated with an ultra thin layer of a conductor, such as gold, and may be selectively tuned to absorb a particular frequency of electromagnetic radiation. In certain such embodiments, the nanoparticles range in size between about 5 nanometers and about 20 nanometers and can be suspended in a suitable material or solution, such as a saline solution. Coatings comprising nanotubes or nanoparticles may also be used to absorb energy from, for example, HIFU, MRI, inductive heating or the like.

In other embodiments, thin film deposition or other coating techniques such as sputtering, reactive sputtering, metal ion implantation, physical vapor deposition, and chemical deposition can be used to cover portions or all of the tissue shaping device. Such coatings can be either solid or microporous. When HIFU energy is used, for example, a microporous structure traps and directs the HIFU energy toward the shape memory material. The coating improves thermal conduction and heat removal. In certain embodiments, the coating also enhances radio-opacity of the tissue shaping device. Coating materials can be selected from various groups of biocompatible organic or non-organic, metallic or non-metallic materials such as Titanium Nitride (TiN), Iridium Oxide (Irox), Carbon, Platinum black, Titanium Carbide (TiC) and other materials used for pacemaker electrodes for implantable pacemaker leads. Other materials discussed herein or known in the art can also be used to absorb energy.

In addition, or in other embodiments, fine conductive wires such as platinum coated copper, titanium, tantalum, stainless steel, gold, or the like, are wrapped around the shape memory material to allow focused and rapid heating of the shape memory material while reducing undesired heating of surrounding tissues.

In certain embodiments, the energy source is applied surgically either during or after implantation. For example, the shape memory material may be heated during implantation of the tissue shaping device by touching the tissue shaping device, or surrounding area, with a warm object or fluid. As another example, the energy source may be surgically applied after the tissue shaping device has been implanted, such as by percutaneously inserting a catheter into the patient's body and applying the energy through the catheter. For example, RF energy, light energy or thermal energy (e.g., from a heating element using resistance heating) can be transferred to the shape memory material through a catheter positioned on or near the shape memory material.

Alternatively, thermal energy can be provided to the tissue shaping device by injecting a heated fluid through a catheter or by circulating the heated fluid in a balloon through the catheter placed in close proximity to the tissue shaping device. As another example, the shape memory material can be coated with a photodynamic absorbing material that is activated to heat the shape memory material when illuminated by light from a laser diode or directed to the coating through fiber optic elements in a catheter. In certain such embodiments, the photodynamic absorbing material may also include one or more drugs that are released when illuminated by the laser light.

In certain embodiments, a removable subcutaneous electrode or coil couples energy from a dedicated activation unit. In certain such embodiments, the removable subcutaneous electrode provides telemetry and power transmission between the system and the tissue shaping device. The subcutaneous removable electrode allows more efficient coupling of energy to the implant with minimum or reduced power loss. In certain embodiments, the subcutaneous energy is delivered via inductive coupling.

In other embodiments, the energy source is applied in a non-invasive, or less invasive, manner from outside the patient's body. In certain such embodiments, the external energy source may be focused to provide directional heating to the shape memory material to reduce or minimize damage to the surrounding tissue. For example, in certain embodiments, a portable device comprising an electrically conductive coil generates an electromagnetic field that non-invasively penetrates the patient's body and induces a current in the tissue shaping device. The current heats the tissue shaping device and causes the shape memory material to transform to a memorized shape. In certain such embodiments, the tissue shaping device also comprises an electrically conductive coil wrapped around or embedded in the memory shape material. The externally generated electromagnetic field induces a current in the tissue shaping device's coil, thereby causing it to heat and transfer thermal energy to the shape memory material.

In certain other embodiments, an external transducer focuses ultrasound energy onto the implanted tissue shaping device to heat the shape memory material. The term "focused ultrasound" as used herein is a broad term and is used in its ordinary sense and includes, without limitation, acoustic energy within a wide range of intensities and/or frequencies. For example, focused ultrasound energy includes high intensity frequency ultrasound (HIFU) energy and/or acoustic energy having an intensity and/or frequency that is considerably less than what is currently used for ablation in medical procedures.

For instance, in certain embodiments, focused ultrasound energy includes acoustic energy within a frequency range of approximately 0.5 MHz to approximately 30 MHz and a power density within the range of approximately 1 W/cm$^2$ and approximately 500 W/cm$^2$. In further embodiments, focused ultrasound energy includes an intensity of acoustic energy that results in non-destructive heating such that little or now tissue damage occurs from the heating and/or such that effects from cavitation are reduced or substantially eliminated.

For exemplary purposes, the term HIFU is used herein with respect to certain embodiments of the invention. However, it is to be understood that other intensities of focused ultrasound energy, and in particular, relatively low intensities of focused ultrasound energy, may advantageously be used in place of, or in combination with, HIFU energy.

In certain embodiments, a HIFU probe is used with an adaptive lens to compensate for heart and respiration movement. The adaptive lens has multiple focal point adjustments. In certain embodiments, a HIFU probe with adaptive capabilities comprises a phased array or linear configuration. In certain embodiments, an external HIFU probe comprises a lens configured to be placed between a patient's ribs to improve acoustic window penetration and reduce or minimize issues and challenges regarding passing through bones. In certain embodiments, HIFU energy is synchronized with an ultrasound imaging device to allow visualization of the tissue shaping device during HIFU activation. In addition, or in other embodiments, ultrasound imaging is used to non-invasively monitor the temperature of tissue surrounding the tissue shaping device by using principles of speed of sound shift and changes to tissue thermal expansion.

In certain embodiments, the tissue shaping device comprises an ultrasound absorbing material or hydro-gel material that allows focused and rapid heating when exposed to the ultrasound energy and transfers thermal energy to the shape memory material.

In certain embodiments, non-invasive energy is applied to the implanted tissue shaping device using a Magnetic Resonance Imaging (MRI) device. In certain such embodiments, the shape memory material is activated by a constant magnetic field generated by the MRI device. In addition, or in other embodiments, the MRI device generates RF pulses that induce current in the tissue shaping device and heat the shape memory material. The tissue shaping device can include one or more coils and/or MRI energy absorbing material to increase the efficiency and directionality of the heating. Suitable energy absorbing materials for magnetic activation energy include particulates of ferromagnetic material. Suitable energy absorbing materials for RF energy include ferrite materials as well as other materials capable of absorbing RF energy at resonant frequencies thereof.

In certain embodiments, the MRI device is further used to determine the size and/or shape of the implanted tissue shaping device before, during and/or after the shape memory material is activated. In certain such embodiments, the MRI device generates RF pulses at a first frequency to heat the shape memory material and at a second frequency to image the implanted tissue shaping device. Thus, the size and/or shape of the tissue shaping device can be measured without heating the device. In certain such embodiments, an MRI energy absorbing material heats sufficiently to activate the shape memory material when exposed to the first frequency and does not substantially heat when exposed to the second frequency. Other imaging techniques known in the art can also be used to determine the size of the implanted device including, for example, ultrasound imaging, computed tomography (CT) scanning, X-ray imaging, position emission tomography (PET) or the like. In certain embodiments, such imaging techniques also provide sufficient energy to activate the shape memory material.

In certain embodiments, activation of the shape memory material is synchronized with the heart beat during an imaging procedure. For example, an imaging technique can be used to focus HIFU energy onto a tissue shaping device in a patient's body during a portion of the cardiac cycle. As the heart beats, the tissue shaping device may move in and out of this area of focused energy. To reduce damage to the surrounding tissue, the patient's body is exposed to the HIFU energy only during select portions of the cardiac cycle. In certain embodiments, the energy is gated with a signal that represents the cardiac cycle, such as an electrocardiogram signal. In certain such embodiments, the synchronization and gating is configured to allow delivery of energy to the shape memory materials at specific times during the cardiac cycle to avoid or reduce the likelihood of causing arrhythmia or fibrillation during vulnerable periods. For example, the energy can be gated so as to only expose the patient's heart to the energy during the T wave of the electrocardiogram signal.

As discussed above, shape memory materials include, for example, polymers, metals, and metal alloys including ferromagnetic alloys. Exemplary shape memory polymers that are usable for certain embodiments of the present invention are disclosed by Langer, et al. in U.S. Pat. No. 6,720,402, issued Apr. 13, 2004, U.S. Pat. No. 6,388,043, issued May 14, 2002, and U.S. Pat. No. 6,160,084, issued Dec. 12, 2000, each of which is hereby incorporated herein by reference in its entirety.

Shape memory polymers respond to changes in temperature by changing to one or more permanent or memorized shapes. In certain embodiments, the shape memory polymer is heated to a temperature between approximately 38° C. and approximately 60° C. In certain other embodiments, the shape memory polymer is heated to a temperature in a range between approximately 40° C. and approximately 55° C. In certain embodiments, the shape memory polymer has a two-way shape memory effect, wherein the shape memory polymer is heated to change it to a first memorized shape and cooled to change it to a second memorized shape. The shape memory polymer can be cooled, for example, by inserting or circulating a cooled fluid through a catheter.

Shape memory polymers implanted in a patient's body can be heated non-invasively using, for example, external light energy sources such as infrared, near-infrared, ultraviolet, microwave and/or visible light sources. Preferably, the light energy is selected to increase absorption by the shape memory polymer and reduce absorption by the surrounding tissue. Thus, damage to the tissue surrounding the shape memory polymer is reduced when the shape memory polymer is heated to change its shape. In other embodiments, the shape memory polymer comprises gas bubbles or bubble containing liquids, such as fluorocarbons, and is heated by inducing a cavitation effect in the gas/liquid when exposed to HIFU energy. In other embodiments, the shape memory polymer may be heated using electromagnetic fields and may be coated with a material that absorbs electromagnetic fields.

Certain metal alloys have shape memory qualities and respond to changes in temperature and/or exposure to magnetic fields. Exemplary shape memory alloys that respond to changes in temperature include alloys of titanium-nickel, copper-zinc-aluminum, copper-aluminum-nickel, iron-manganese-silicon, iron-nickel-aluminum, gold-cadmium, combinations of the same, and the like.

Shape memory alloys can exist in at least two distinct solid phases called martensite and austenite. In the martensite phase, the alloy is relatively soft and easily deformed, whereas in the austenite phase, the alloy is relatively stronger and less easily deformed. For example, shape memory alloys generally enter the austenite phase at a higher temperature relative to entering the martensite phase. Shape memory alloys begin transforming to the martensite phase at a start temperature ($M_s$) and finish transforming to the martensite phase at a finish temperature ($M_f$). Similarly, such shape memory alloys begin transforming to the austenite phase at a start temperature ($A_s$) and finish transforming to the austenite phase at a finish temperature ($A_f$). In general, both transformations have a hysteresis. Thus, the $M_s$ temperature and the $A_f$ temperature are not coincident with each other, and the $M_f$ temperature and the $A_s$ temperature are not coincident with each other.

In certain embodiments, the shape memory alloy is processed to form a memorized arcuate shape in the austenite phase. The shape memory alloy is then cooled below the $M_f$ temperature to enter the martensite phase and deformed into a different configuration, such as a second arcuate shape having more or less of a curve. In certain embodiments, the shape memory alloy is sufficiently malleable in the martensite phase to allow a user such as a physician to adjust the shape of the device in the martensite phase by hand to achieve a desired fit for a particular patient. After the device is positioned within the coronary sinus, the shape of the device can be adjusted non-invasively by heating the shape memory alloy to an activation temperature (e.g., temperatures ranging from the $A_s$ temperature to the $A_f$ temperature).

Thereafter, when the shape memory alloy is exposed to a temperature elevation and transformed to the austenite phase, the alloy changes in shape from the deformed shape to the memorized shape. Activation temperatures at which the shape memory alloy causes the shape of the tissue shaping device to change shape can be selected for the tissue shaping device such that collateral damage is reduced or eliminated in tissue adjacent the device during the activation process. In certain embodiments, exemplary $A_f$ temperatures for suitable shape memory alloys range between approximately 45° C. and approximately 50° C., and exemplary $A_s$ temperatures range between approximately 42° C. and approximately 53° C. Furthermore, exemplary $M_s$ temperatures range between approximately 10° C. and approximately 20° C., and exemplary $M_f$ temperatures range between approximately −1° C. and approximately 15° C. The shape of the tissue shaping device can change substantially instantaneously or incrementally in small steps in order to achieve the adjustment necessary to produce the desired clinical result.

Certain shape memory alloys may further include a rhombohedral phase, having a rhombohedral start temperature ($R_s$) and a rhombohedral finish temperature ($R_f$), that exists between the austenite and martensite phases. An example of such a shape memory alloy is a NiTi alloy, which is commercially available from Memry Corporation (Bethel, Connecticut). In certain embodiments, an exemplary $R_s$ temperature range is between approximately 30° C. and approximately 50° C., and an exemplary $R_f$ temperature range is between approximately 20° C. and approximately 35° C. One benefit of using a shape memory material having a rhombohedral phase is that in the rhomobohedral phase the shape memory material may experience a partial physical distortion, as compared to the generally rigid structure of the austenite phase and the generally deformable structure of the martensite phase.

Certain shape memory alloys exhibit a ferromagnetic shape memory effect, wherein the shape memory alloy transforms from the martensite phase to the austenite phase when exposed to a magnetic field. Thus, a tissue shaping device comprising a ferromagnetic shape memory alloy may be implanted in a first configuration having a first shape and later changed to a second configuration having a second (e.g., memorized) shape without heating the shape memory material above the As temperature. Advantageously, nearby healthy tissue is not exposed to high temperatures that could damage the tissue. Furthermore, since the ferromagnetic shape memory alloy does not need to be heated, the size and/or shape of the tissue shaping device can be adjusted more quickly and more uniformly than by heat activation.

Exemplary ferromagnetic shape memory alloys include Fe—C, Fe—Pd, Fe—Mn—Si, Co—Mn, Fe—Co—Ni—Ti, Ni—Mn—Ga, Ni$_2$MnGa, Co—Ni—Al and the like. Certain of these shape memory materials may also change shape in response to changes in temperature. Thus, the shape of such materials can be adjusted by exposure to a magnetic field, by changing the temperature of the material, or both.

In certain embodiments, combinations of different shape memory materials are used. For example, tissue shaping devices according to certain embodiments comprise a combination of shape memory polymer and shape memory alloy (e.g., NiTi). In certain such embodiments, a tissue shaping device comprises a shape memory polymer body and a shape memory alloy (e.g., NiTi) disposed within the body. Such embodiments are flexible and allow the size and shape of the shape memory alloy to be further reduced without impacting fatigue properties. In addition, or in other embodiments, shape memory polymers are used with shape memory alloys to create a bi-directional (e.g., capable of expanding and contracting) tissue shaping device. Bi-directional tissue shaping devices can be created with a wide variety of shape memory material combinations having different characteristics.

In certain embodiments, the tissue shaping device includes at least one electromagnetic material configured to be activated to dynamically change the shape and/or size of the tissue shaping device. For example, the electromagnetic material, when activated, may interact with another portion of the tissue shaping device, such as a permanent magnet or other ferromagnetic material, to change the shape of the device. In one embodiment, the electromagnetic material is activated by an electromagnetic transmitter, such as a resistive coil, located outside the body of the patient.

The term "ferromagnetic" as used herein is a broad term and is used in its ordinary sense and includes, without limitation, any material that easily magnetizes, such as a material having atoms that orient their electron spins to conform to an external magnetic field. Ferromagnetic materials include permanent magnets, which can be magnetized through a variety of modes, and materials, such as metals, that are attracted to permanent magnets. Ferromagnetic materials also include electromagnetic materials that are capable of being activated by an electromagnetic transmitter, such as one located outside the heart of a patient.

Furthermore, ferromagnetic materials may include one or more polymer-bonded magnets, wherein magnetic particles are bound within a polymer matrix, such as a biocompatible polymer. The magnetic materials can comprise isotropic and/or anisotropic materials, such as for example NdFeB (Neodynium Iron Boron), SmCo (Samarium Cobalt), ferrite and/or AlNiCo (Aluminum Nickel Cobalt) particles. The biocompatible polymer can comprise, for example, polycarbonate, silicone rubber, polyurethane, silicone elastomer, a flexible or semi-rigid plastic, combinations of the same and the like.

In the following description, reference is made to the accompanying drawings, which form a part hereof, and which show, by way of illustration, specific embodiments or processes in which the invention may be practiced. Where possible, the same reference numbers are used throughout the drawings to refer to the same or like components. In some instances, numerous specific details are set forth in order to provide a thorough understanding of the present disclosure. The present disclosure, however, may be practiced without the specific details or with certain alternative equivalent components and methods to those described herein. In other instances, well-known components and methods have not been described in detail so as not to unnecessarily obscure aspects of the present disclosure.

FIG. 1 illustrates a human heart 100 with the atria removed to expose a mitral (left atrioventricular) valve 102 and a coronary sinus 104. Also generally shown in FIG. 1 are a pulmonary valve 106, an aortic valve 108, and a tricuspid valve 110 of the heart 100.

The mitral valve 102 includes an anterior (aortic) leaflet 112, a posterior leaflet 114 and an annulus 116. When healthy, the mitral valve annulus 116 encircles the leaflets 112, 114 and maintains their spacing to provide closure during left ventricular contraction. The coronary sinus 104 partially encircles the mitral valve 102 substantially adjacent to the mitral valve annulus 116 and extends from an ostium 118, or opening to the right atrium, to the anterior interventricular ("AIV") sulcus or groove. In general, the coronary sinus 104 is located within the same plane as the mitral valve annulus 116, which makes the coronary sinus 104 available for placement therein of a tissue shaping device 120.

The tissue shaping device 120 is advantageously sized to fit within the desired vessel or tissue. With reference to FIG. 1, the tissue shaping device 120 is of a size that allows for insertion in or removal from the coronary sinus 104, such as through the use of an elongate tubular device, such as a catheter. In one embodiment, the tissue shaping device 120 has a length between approximately 4 mm and 150 mm. In a preferred embodiment, the tissue shaping device 120 has a length of approximately 50 mm. The tissue shaping device 120, in one embodiment, has a diameter of approximately 2 to 6 mm. In a preferred embodiment, the tissue shaping device 120 has a diameter of approximately 5 mm.

The tissue shaping device 120 illustrated in FIG. 1 is a dynamically adjustable device usable to reshape or resize the mitral valve annulus 116 according to the needs of the patient. In one embodiment, the tissue shaping device 120 can be adjusted in vivo after implantation into a patient's body. In particular, the tissue shaping device 120 is advantageously capable of affecting the shape of the coronary sinus 104, which, in turn, affects the shape of the mitral valve annulus 116. Appropriately affecting the shape of the mitral valve annulus 116 aids closure of the leaflets 112, 114 to improve coaptation, thereby correcting mitral valve insufficiency.

Figure 2A:
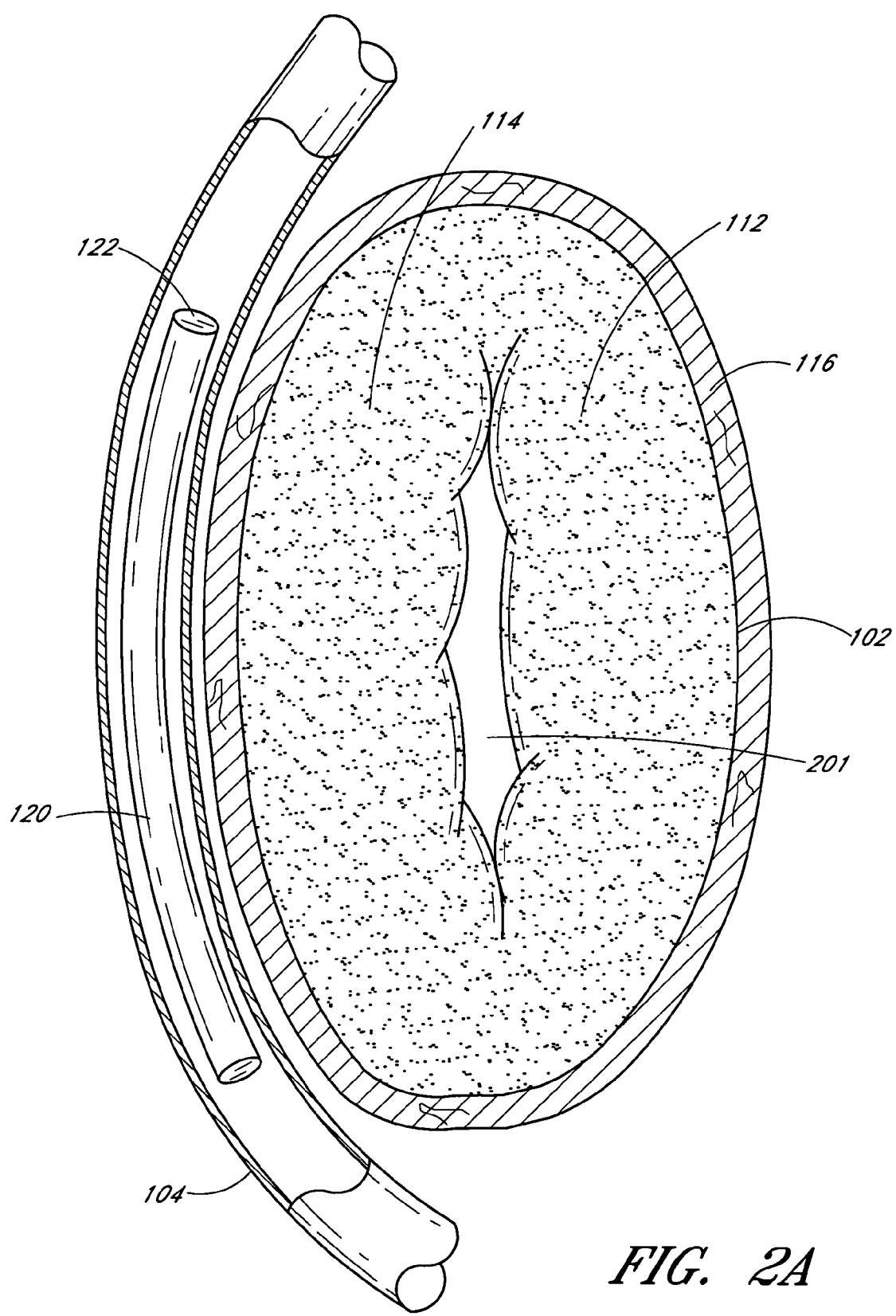
FIGS. 2A and 2B illustrate perspective views of a partial section of the heart including a mitral valve and a coronary sinus with an exemplifying embodiment of a tissue shaping device positioned therein.
Figure 2B:
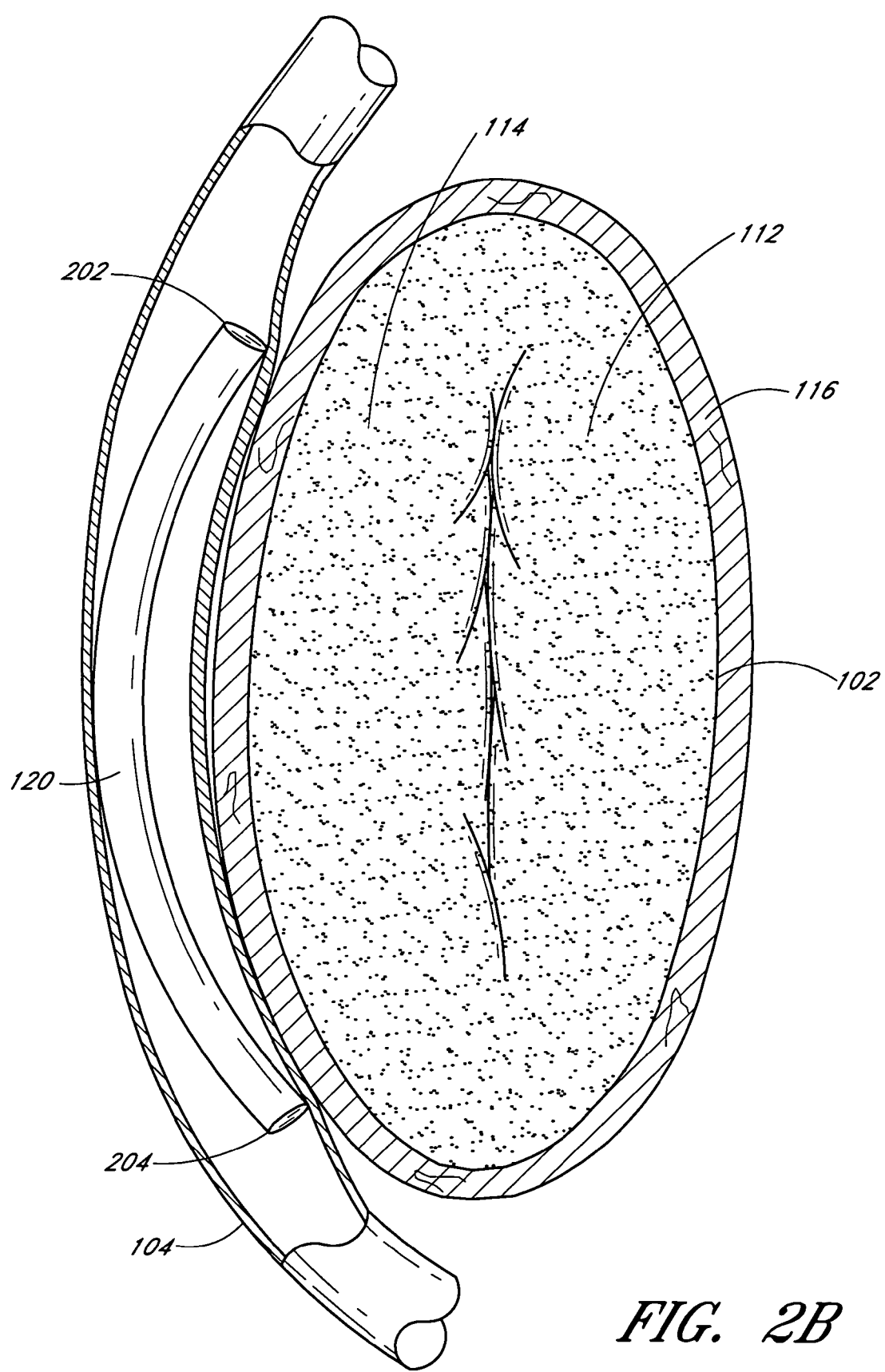

FIG. 2A illustrates a schematic view of the tissue shaping device 120 deployed within the coronary sinus 104. For simplification purposes, FIG. 2A illustrates only the mitral valve 102 and the coronary sinus 104 of the heart 100. As illustrated, a gap 201 exists between the leaflets 112, 114 due to insufficient closure of the leaflets 112, 114. As discussed above, this insufficient closure of the leaflets 112, 114 of the mitral valve 102 may be due to incomplete coaptation of the valve leaflets 112, 114 and can cause regurgitation of the blood, accumulation of blood in the heart and other health problems As illustrated in FIG. 2A, the tissue shaping device 120 is in a first configuration having a slightly arcuate shape. In one embodiment, this arcuate shape is selected to advantageously facilitate placement of the tissue shaping device 120 within the coronary sinus 104. FIG. 2B illustrates the tissue shaping device 120 in a second configuration having an arcuate shape with a greater curvature than the arcuate shape of the first configuration.

As shown in the second configuration, ends 202, 204 of the tissue shaping device 120 contact and apply pressure against the wall of the coronary sinus 104. This pressure causes at least one section of the coronary sinus 104 to push against the annulus 116 of the mitral valve 102, which causes a modification of the shape of the mitral valve annulus 116. In particular, the deformation of the tissue shaping device 120 advantageously moves the posterior leaflet 114 of the mitral valve 102 toward the anterior leaflet 112 to facilitate greater coaptation.

In one embodiment, the tissue shaping device 120 causes a pressure or force of approximately 2.22 newtons (0.5 pound-force) to approximately 13.34 newtons (3.0 pound-force) of displacement on the wall of the coronary sinus 104 in order to change at least one dimension of the mitral valve 102. Such pressure may cause the posterior leaflet 104 to move a distance of between approximately 5 mm and approximately 15 mm toward the anterior leaflet 112. In other embodiments, the posterior leaflet 114 moves a distance between approximately 2 mm and approximately 30 mm toward the anterior leaflet 112.

Figure 3A:
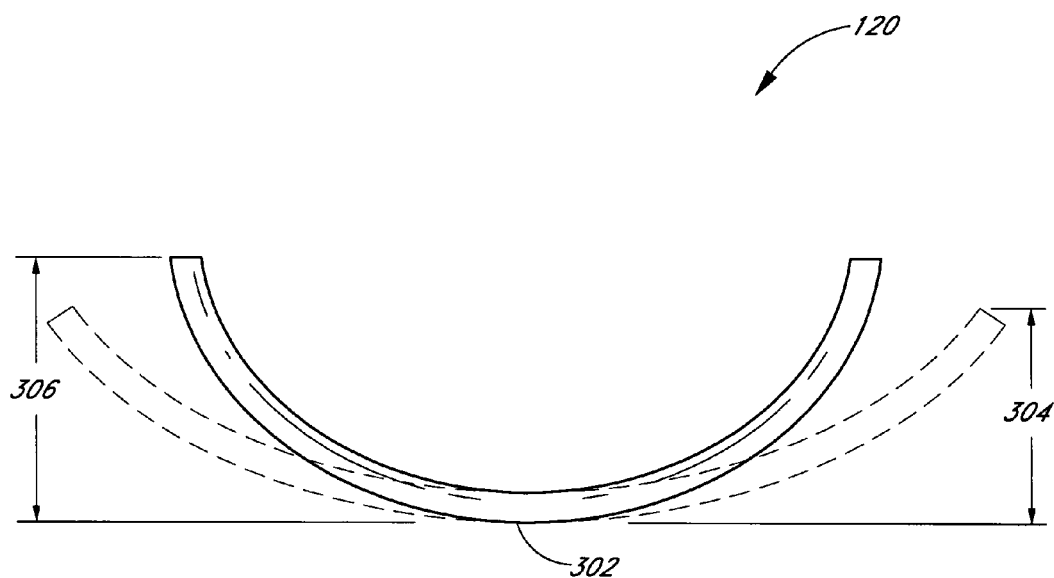
FIGS. 3A and 3B illustrate perspective views of exemplary configurations of an adjustable tissue shaping device according to certain embodiments of the invention.

FIG. 3A illustrates an exemplary embodiment of the arcuately-shaped tissue shaping device 120 capable of contracting from a first configuration to a second configuration. The tissue shaping device 120 is illustrated in the first configuration by dashed (phantom) lines and has a generally parabolic shape including a vertex 302 and a first vertical dimension 304. In certain embodiments, the tissue shaping device 120 has a length of between approximately 3 millimeters and approximately 30 millimeters. In further embodiments, the tissue shaping device 120 advantageously has a length of between approximately 3 millimeters and approximately 10 millimeters. In certain embodiments, the vertical dimension 304 has a length between 0 millimeters (e.g., a substantially straight tissue shaping device 120) and approximately 3.0 millimeters.

In the first configuration, the tissue shaping device 120 has not yet contracted. For example, the tissue shaping device 120 may assume the first configuration when initially positioned within the coronary sinus 104 prior to reshaping of the mitral valve annulus 116. In one embodiment, the first configuration may correspond to the configuration of the tissue shaping device 120 depicted in FIG. 2A.

FIG. 3A further illustrates the tissue shaping device 120 contracted to a second configuration (represented by the solid lines). In one embodiment, the tissue shaping device 120 is adjustable to the second configuration in order to dynamically reshape or reform the mitral valve annulus 116. In particular, in the second configuration, the tissue shaping device 120 has a second vertical dimension 306, which is illustrated as being longer than the first vertical dimension 304. In one embodiment, the second vertical dimension 306 has a length that is between approximately 0.01 millimeter and approximately 10 millimeters. In more preferred embodiments, the second vertical dimension has a length that is between approximately 0.05 millimeter and approximately 5 millimeters.

As shown, the second configuration also results in the tissue shaping device 120 having a sharper curve with the ends 202, 204 moved closer together. In one embodiment, the second configuration advantageously causes the vertex 302 to contact a portion of the coronary sinus 104 and at least one of the ends 202, 204 to contact an opposing portion of the coronary sinus 104. The resulting pressure provided by the tissue shaping device 120 causes the reforming of the mitral valve annulus 116.

Figure 3B:
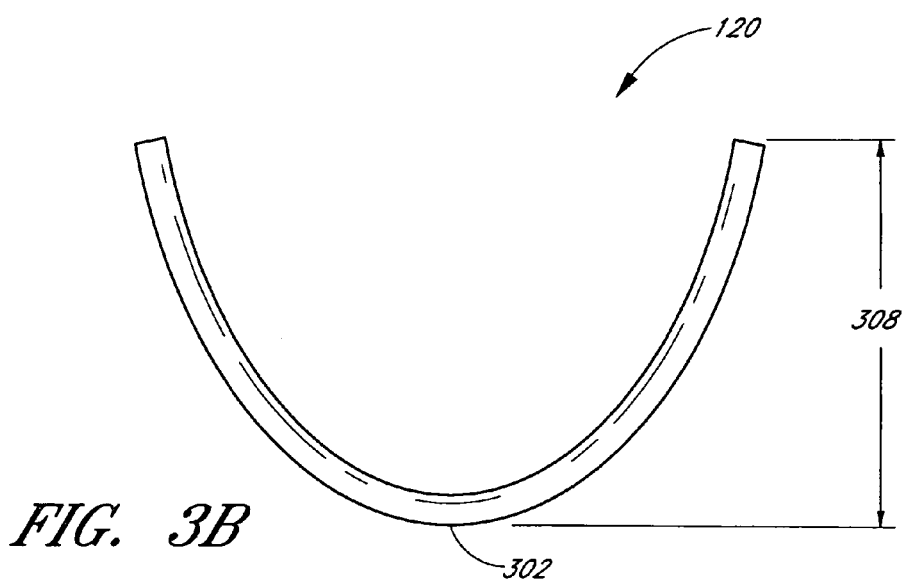

FIG. 3B illustrates a further embodiment of the tissue shaping device 120, wherein the tissue shaping device 120 is adjustable to a third configuration. In such a configuration, the tissue shaping device 120 has a third vertical dimension 308, which is illustrated as being longer than the first vertical dimension 304 and the second vertical dimension 306 depicted in FIG. 3A. In such embodiments, the third configuration is advantageously usable to cause an increased pressure on the wall of the coronary sinus 104 and a corresponding pressure on the mitral valve annulus 116.

Although described with reference to particular embodiments, the tissue shaping device 120 may take on other forms or configurations that are suitable for reshaping tissue. For example, embodiments of the tissue shaping device 120 may transform between only two configurations (e.g., at the austenite and martensite phases), or the tissue shaping device 120 may experience transformations between more than three configurations. Furthermore, other embodiments of the tissue shaping device 120 may experience changes in dimensions other than, or in combination with, an increase in the vertical dimension of the tissue shaping device 120. For example, only a select segment of the tissue shaping device 120 may undergo a shape transformation, such as, for example, a segment consisting essentially of a shape memory material.

Deformation of the tissue shaping device 120 from at least the first configuration to the second configuration may be performed in several ways. In certain embodiments, the tissue shaping device 120 comprises a shape memory material that is responsive to changes in temperature and/or exposure to a magnetic field. With reference to FIGS. 3A and 3B, in certain embodiments, the tissue shaping device 120 includes at least one shape memory portion usable to adjust the tissue shaping device 120 from the first configuration to the second configuration. For example, the first configuration may correspond to when the shape memory portion is in the martensite phase, and the second configuration may correspond to when the shape memory portion is in the austenite phase. In other embodiments, the second configuration may correspond to when the shape memory material is in the rhombohedral phase, and the third configuration may correspond to when the shape memory material is in the austenite phase.

As discussed above, the shape memory material may include shape memory polymers (e.g., polylactic acid (PLA), polyglycolic acid (PGA)) and/or shape memory alloys (e.g., nickel-titanium) including, for example, ferromagnetic shape memory alloys (e.g., Fe—C, Fe—Pd, Fe—Mn—Si, Co—Mn, Fe—Co—Ni—Ti, Ni—Mn—Ga, $Ni_2MnGa$, Co—Ni—Al). In certain such embodiments, the tissue shaping device 120 is adjusted in vivo by applying an energy source such as, but not limited to, radio frequency energy, X-ray energy, microwave energy, acoustic energy such as HIFU energy, light energy, electric field energy, magnetic field energy, combinations of the same or the like.

Preferably, the energy source is applied in a non-invasive manner from outside the body of the patient, as is described in more detail herein. For example, a magnetic field and/or RF pulses can be applied to the tissue shaping device 120 within the coronary sinus 104 of a patient with an apparatus external to the coronary sinus or the patient's heart and/or unattached to the tissue shaping device 120. Such magnetic fields and/or RF pulses are commonly used for magnetic resonance imaging (MRI). However, in other embodiments, the energy source may be applied surgically, such as by inserting a catheter into the body and applying energy through the catheter.

In certain embodiments, the tissue shaping device 120 is selectively heated using short pulses of energy having an on and an off period between each cycle. The energy pulses provide segmental heating which allows segmental adjustment of portions of the tissue shaping device 120 without adjusting the entire implant.

In certain embodiments, the tissue shaping device 120 comprises a shape memory material that responds to a change in temperature that differs from a nominal ambient temperature, such as the nominal body temperature of 37° C. for humans. For example, the tissue shaping device 120 may be configured to respond by starting to contract upon heating of the tissue shaping device 120 above the $A_s$ temperature of the shape memory material.

The activation temperatures (e.g., temperatures ranging from the $A_s$ temperature to the $A_f$ temperature) at which the tissue shaping device 120 contracts (e.g., increased vertical dimension) may be selected for the tissue shaping device 120 such that collateral damage is reduced or eliminated in tissue adjacent the tissue shaping device 120 during the activation process. Exemplary $A_f$ temperatures for the shape memory material of the tissue shaping device 120 at which substantially maximum contraction occurs are in a range between approximately 38° C. and approximately 75° C. For some embodiments that include shape memory polymers for the tissue shaping device 120, activation temperatures at which the glass transition of the material or substantially maximum contraction occur range between approximately 38° C. and approximately 60° C. In other such embodiments, the activation temperature is in a range between approximately 45° C. and approximately 50° C.

In certain embodiments, the tissue shaping device 120 is shape set in the austenite phase to a remembered configuration during the manufacturing of the tissue shaping device 120 such that the remembered configuration is arcuately shaped and has a relatively long vertical dimension. After cooling the tissue shaping device 120 below the $M_f$ temperature, the tissue shaping device 120 is manually deformed into a shape having a shorter vertical dimension. In certain such embodiments, the tissue shaping device 120 is sufficiently malleable in the martensite phase to allow a user such as a physician to adjust the shape by hand to achieve a desired fit with the corresponding coronary sinus 104 and mitral valve 102 of the patient. In certain embodiments, the starting shape of the tissue shaping device 120 is selected to improve leaflet coaptation and reduce regurgitation in the mitral valve 102.

For embodiments of the tissue shaping device 120 made from a continuous piece of shape memory alloy (e.g., NiTi alloy) or shape memory polymer, the tissue shaping device 120 can be activated by the surgical and/or non-invasive application of heating energy by the methods discussed above. For embodiments of the tissue shaping device 120 made from a continuous piece of ferromagnetic shape memory alloy, the tissue shaping device 120 can be activated by the non-invasive application of a suitable magnetic field.

Alternatively, the tissue shaping device 120 may comprise two or more sections or zones of shape memory material having different temperature response curves. The shape memory response zones may be configured in order to achieve a desired configuration of the tissue shaping device 120 when in a contracted state, either fully contracted or partially contracted.

The shape modification process of the tissue shaping device 120, either non-invasively or through a catheter, can be carried out all at once or incrementally in order to produce the desired clinical result. If heating energy is applied such that the temperature of the tissue shaping device 120 does not reach the $A_f$ temperature for substantially maximum transition contraction, partial shape memory transformation and contraction may occur.

In certain embodiments, the shape memory portion of the tissue shaping device 120 extends more than half the length of the tissue shaping device 120. In embodiments of the invention having multiple shape memory portions, the total length of the shape memory portions may exceed half the length of the tissue shaping device 120 while one or more of the multiple portions may have an individual length of less than half the length of the tissue shaping device 120.

The shape modification process of the tissue shaping device 120, either non-invasively or through a catheter, can be carried out all at once or incrementally in order to produce the desired clinical result. If heating energy is applied such that the temperature of the tissue shaping device 120 does not reach the $A_f$ temperature for substantially maximum transition contraction, partial shape memory transformation and contraction may occur.

After implantation, the tissue shaping device 120 is preferably activated non-invasively by the application of energy to the patient's body to heat the tissue shaping device 120. In certain embodiments, an MRI device is used as discussed above to heat the tissue shaping device 120, which then causes the shape memory material of the tissue shaping device 120 to transform to the austenite phase and its associated (contracted) configuration. Thus, the shape of the tissue shaping device 120 is changed in vivo without the need for surgical intervention. Standard techniques for focusing the magnetic field from the MRI device onto the tissue shaping device 120 may be used. For example, a conductive coil can be wrapped around the patient in an area corresponding to the tissue shaping device 120. In other embodiments, the shape memory material is activated by exposing it other sources of energy, as discussed above.

Figure 4:
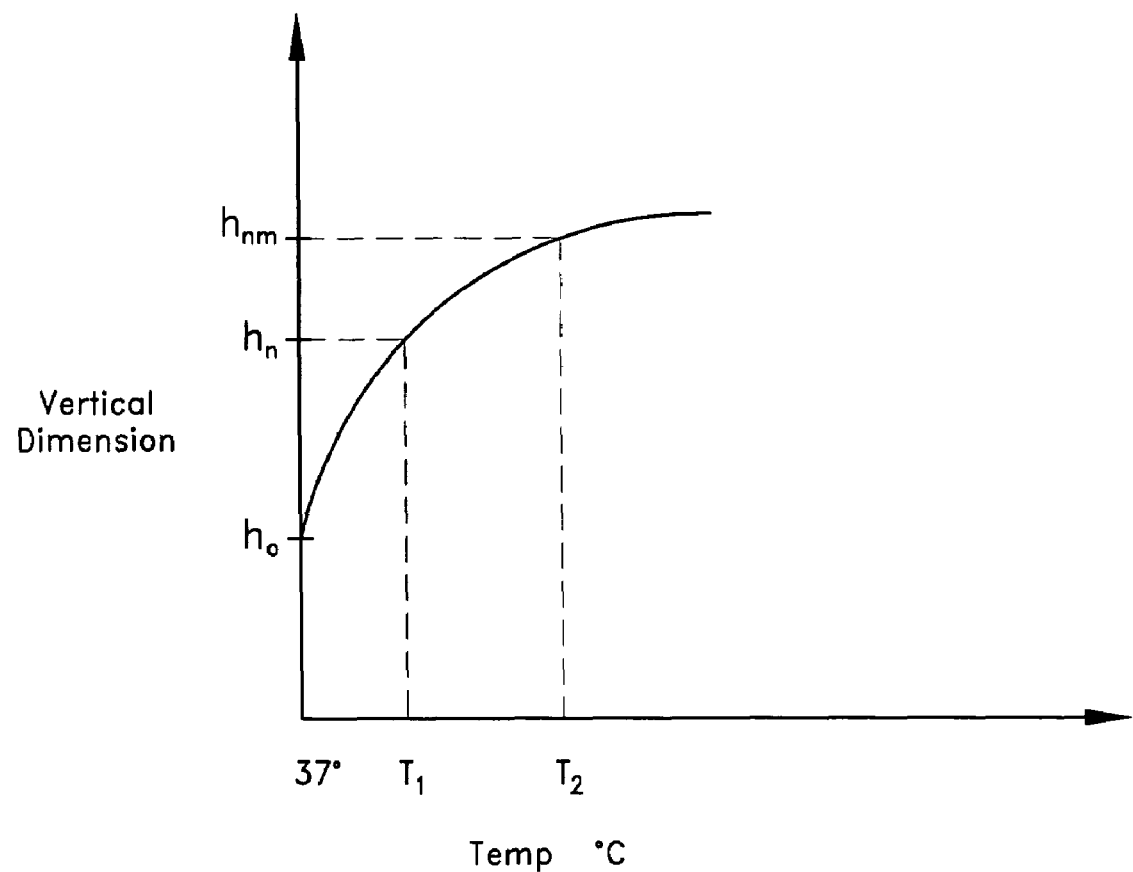
FIG. 4 is a graphical representation of the change in shape of a tissue shaping device in relation to the temperature of the tissue shaping device according to certain embodiments of the invention.

FIG. 4 graphically illustrates the relationship between the temperature and vertical dimension of the tissue shaping device 120 according to certain embodiments. Although the term "vertical dimension" is used herein to characterize the general shape and size of the tissue shaping device 120 (e.g., the distance between a portion of the body of the tissue shaping device 120 and a line intersecting both ends of the tissue shaping device 120), other terms and/or measurements may be used for describing the shape, curvature and/or size of the tissue shaping device 120. For example, the change in the shape, curvature and/or size of the tissue shaping device 120 may be characterized through changes in a radius, a focal length, a height, a width, a length or like dimension of the tissue shaping device 120.

With reference to FIG. 4, at body temperature of approximately 37° C., the vertical dimension of the tissue shaping device 120 is equal to a first vertical dimension $h_0$. In certain embodiments, the tissue shaping device 120 comprises a shape memory material that is then increased to a first raised temperature $T_1$. In response, the vertical dimension of the tissue shaping device 120 increases to a second vertical dimension $h_n$. The vertical dimension of the tissue shaping device 120 can then be increased to a third vertical dimension $h_{nm}$ by raising the temperature to a second raised temperature $T_2$.

As graphically illustrated in FIG. 4, in certain embodiments, the change in vertical dimension from $h_0$ to $h_{nm}$ is substantially continuous as the temperature is increased from body temperature to $T_2$. For example, in certain embodiments a magnetic field of about 2.5 Tesla to about 3.0 Tesla is used to raise the temperature of the tissue shaping device 120 above the $A_f$ temperature to complete the austenite phase and return the tissue shaping device 120 to the remembered configuration (e.g., second configuration illustrated in FIG. 2B) with the longer vertical dimension. However, a lower magnetic field (e.g., 0.5 Tesla) can initially be applied and increased (e.g., in 0.5 Tesla increments) until the desired level of heating and desired contraction of the tissue shaping device 120 is achieved. In other embodiments, the tissue shaping device 120 comprises a plurality of shape memory materials with different activation temperatures, and the vertical dimension of the tissue shaping device 120 is increased in steps as the temperature increases.

Whether the shape change is continuous or stepped, the contraction of the tissue shaping device 120 can be assessed or monitored using MRI imaging, ultrasound imaging, computed tomography (CT) scan, X-ray or the like. If magnetic energy is being used to activate contraction of the tissue shaping device 120, for example, MRI imaging techniques can be used that produce a field strength that is lower than that required for activation of the tissue shaping device 120.

Figure 5:
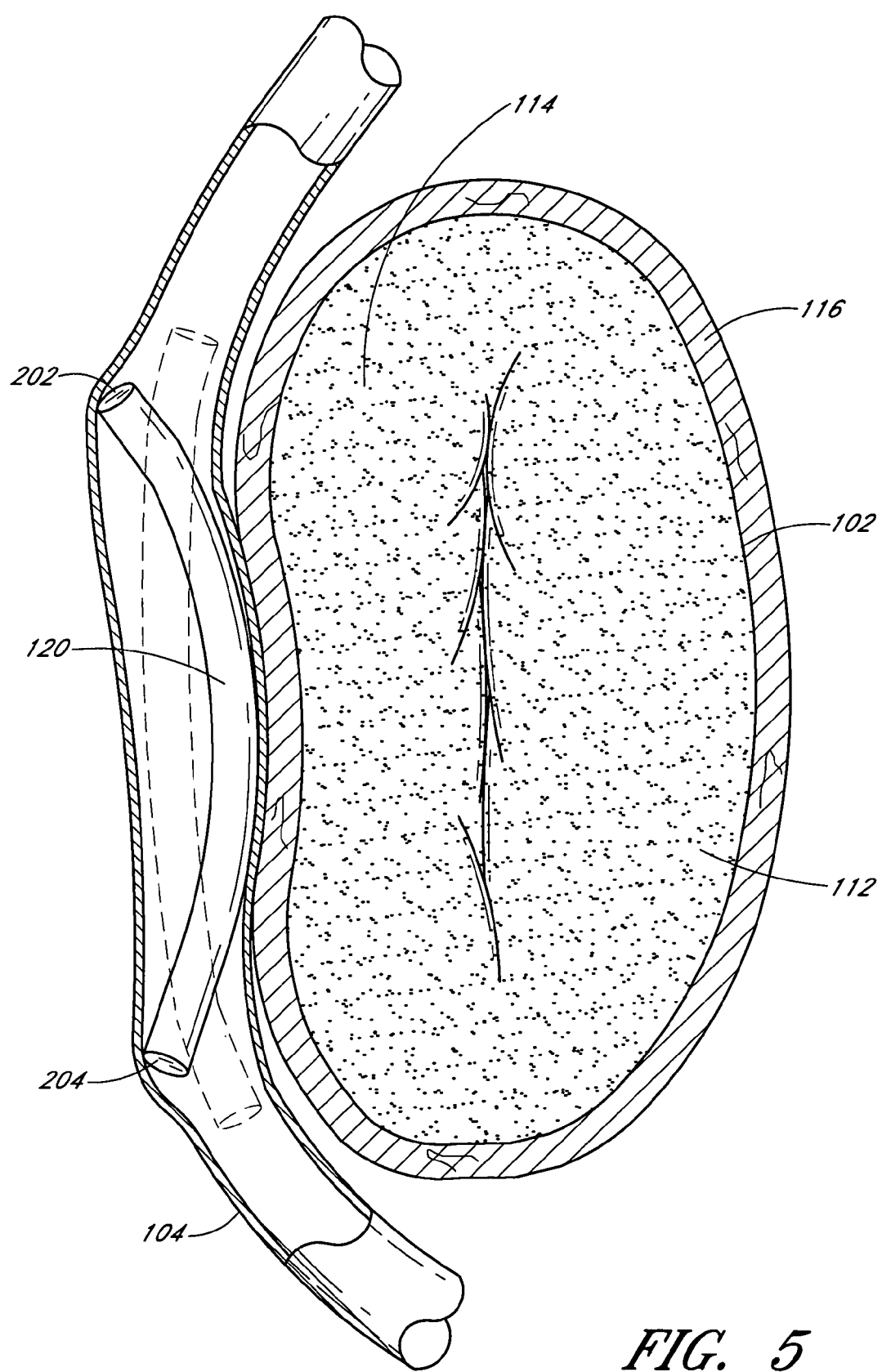
FIG. 5 illustrates a perspective view of a partial section of the heart including a mitral valve and a coronary sinus with another exemplifying embodiment of a tissue shaping device positioned therein.

FIG. 5 depicts another exemplifying embodiment of the tissue shaping device 120 that forms an arcuate shape to cause a section of the wall of the coronary sinus 104 to push outward in the general direction of the mitral valve annulus 116. In particular, the tissue shaping device 120 dynamically adjusts such that a convex portion or side of the tissue shaping device 120 bows toward the mitral valve annulus 116, which causes movement of the posterior leaflet 114 toward the anterior leaflet 112 to facilitate greater coaptation. The broken line depicted in FIG. 5 illustrates the shape of the tissue shaping device 120 prior to deformation (e.g., pre-implant).

In other embodiments of the invention, the tissue shaping device 120 may have different shapes or forms than the generally tubular shape depicted in FIGS. 1-3 and 5. For example, the tissue shaping device 120 may comprise a helical shape, an arcuate shape, an S-shape, a ribbon-like shape, a curvilinear shape, a braided-wire, multiple wires, combinations of the same or the like.

Figure 6:
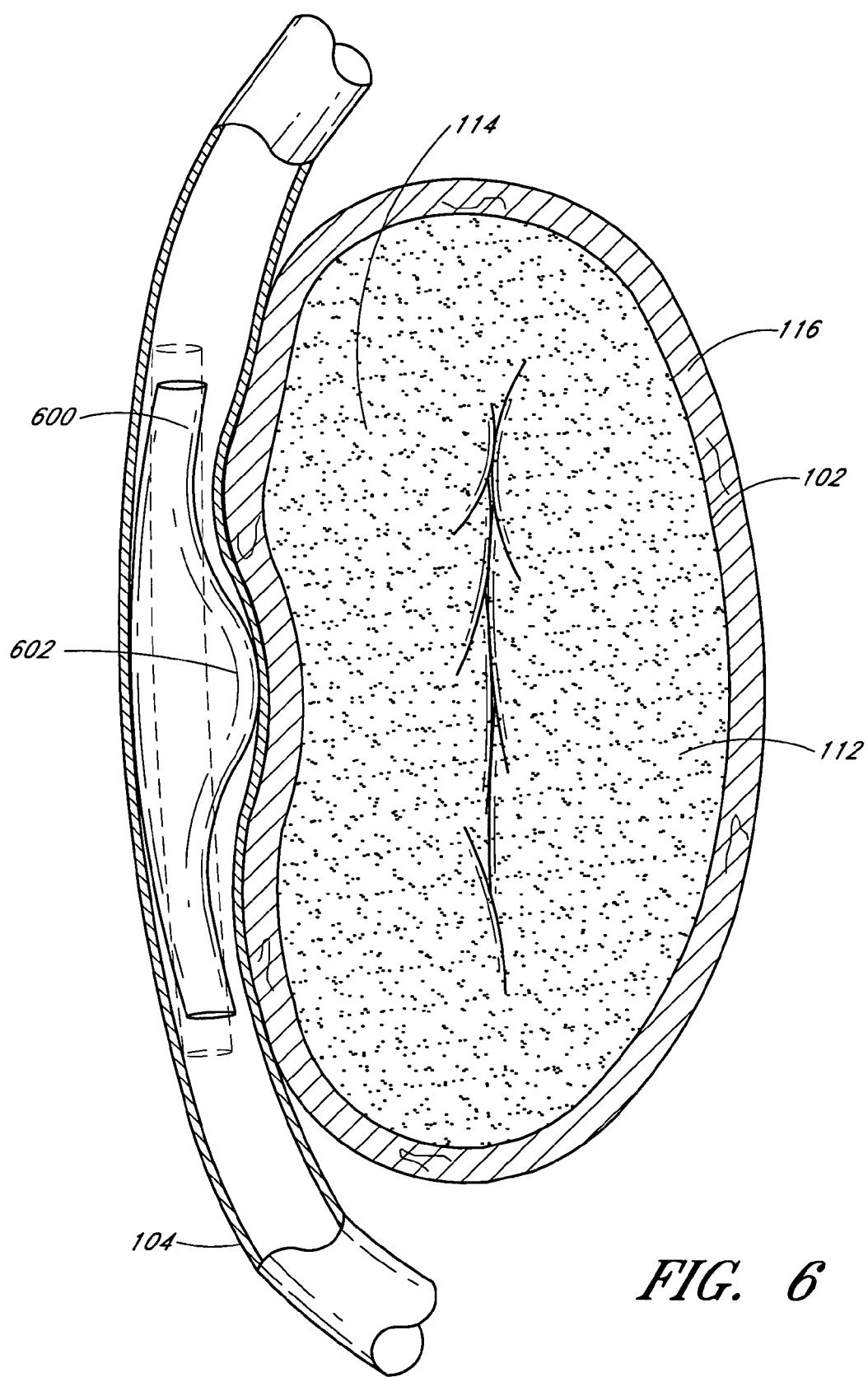
FIG. 6 illustrates a perspective view of a partial section of the heart including a mitral valve and a coronary sinus with another exemplifying embodiment of a tissue shaping device positioned therein.

FIG. 6 illustrates another exemplifying embodiment of a tissue shaping device 600 that is dynamically adjustable to effect changes in at least one dimension of the mitral valve annulus 116. The tissue shaping device 600 has a generally uniform tubular shape in a first configuration, as shown by the dashed lines. In a second configuration, the tissue shaping device 600 forms a protrusion 602 near the center of the length of the tissue shaping device 600. In one embodiment, the protrusion 602 advantageously contacts and pushes against the coronary sinus wall to reshape the mitral valve annulus 116, thereby causing movement of the posterior leaflet 114 toward the anterior leaflet 112 to facilitate greater coaptation.

Although disclosed with reference to particular embodiments, the tissue shaping device 600 may take on alternative forms and/or shapes during dynamic adjustments between multiple configurations. For example, the tissue shaping device 600 may include multiple protrusions or may take on an arcuate shape in the second configuration, similar to the shape of the tissue shaping device 120 depicted in FIG. 2B.

Figure 7:
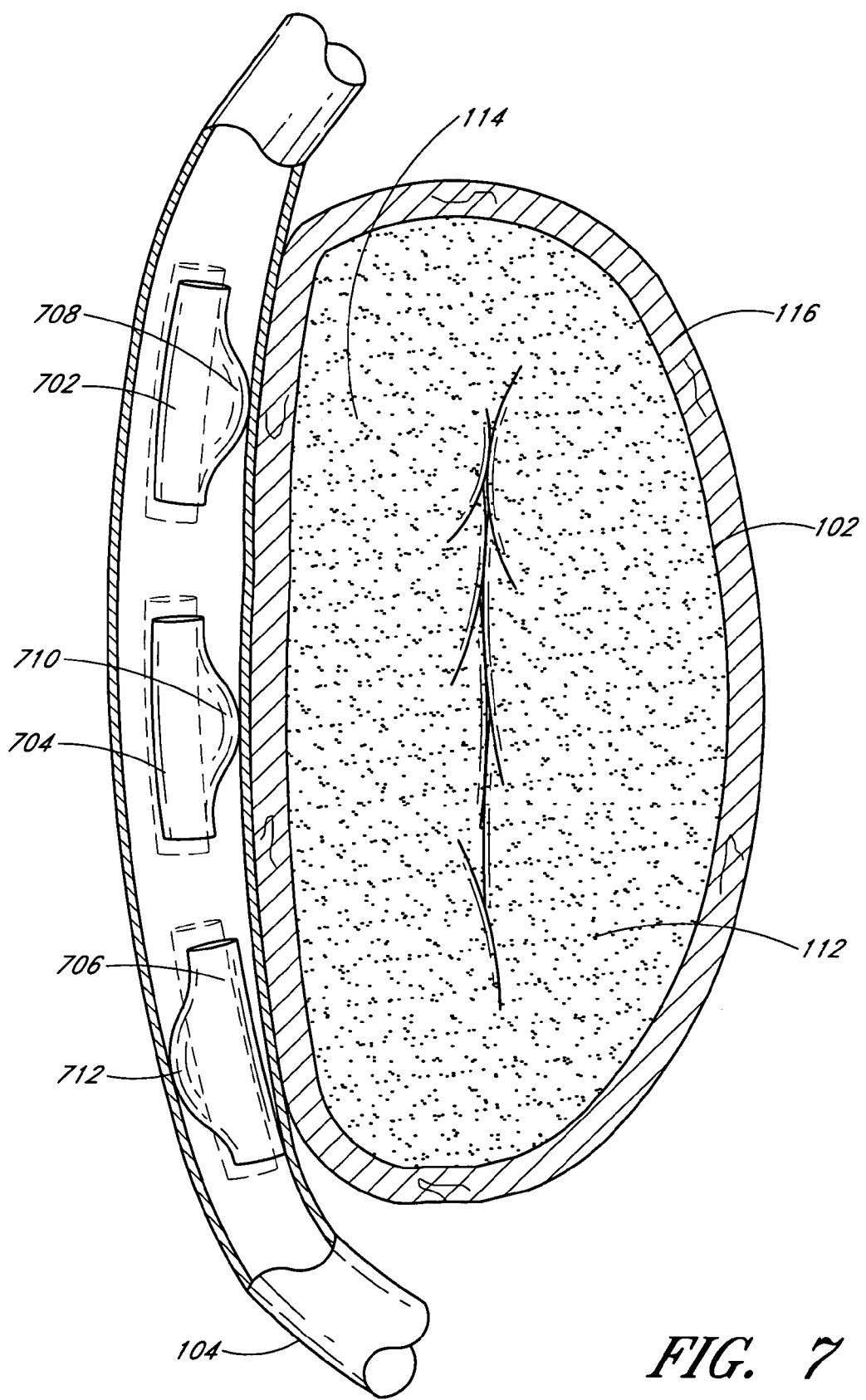
FIG. 7 illustrates a perspective view of a partial section of the heart including a mitral valve and a coronary sinus with multiple tissue shaping devices positioned therein according to certain embodiments of the invention.

FIG. 7 illustrates an embodiment of the invention that provides for multiple implants having differing strengths or effects on the mitral valve annulus 116. In particular, a first tissue shaping device 702, a second tissue shaping device 704 and a third tissue shaping device 706 are positioned within the coronary sinus 104. In the depicted embodiment, the first tissue shaping device 702 develops a protrusion 708 in the second configuration, and the second tissue shaping device 704 develops a protrusion 710 in the second configuration, wherein both the protrusions 708, 710 exert pressure on a coronary sinus 104 wall proximate the mitral valve annulus 116.

The illustrated third tissue shaping device 706 develops a protrusion 712 in the second configuration, wherein the protrusion 712 contacts the coronary sinus wall in a location substantially opposite the mitral valve annulus 116. In one embodiment, the tissue shaping devices 702, 704, 706 are configured to exert different pressures on their respective locations on the coronary sinus 104 so as to reform the mitral valve 102 as needed. As illustrated, the tissue shaping device 702, 706 are configured to exert pressure onto the coronary sinus 104 in the direction of the mitral valve 102, while the tissue shaping device 706 is configured to exert pressure on the coronary sinus 104 opposite the mitral valve 102.

Although described with reference to particular embodiments, alternative configurations, shapes, sizes and the like may be used with at least one of the multiple tissue shaping devices 702, 704, 706. In yet other embodiments, additional or fewer tissue shaping devices may be used to achieve a certain therapeutic outcome with respect to the mitral valve 102. In yet other embodiments, the tissue shaping devices 702, 704 may be positioned side-by-side in a parallel configuration to effect corresponding changes in the mitral valve annulus 116. In yet other embodiments, the tissue shaping devices 702, 704, 706 may be of different lengths, different shapes, or otherwise modified to provide for variable forces upon the coronary sinus 104 and the mitral valve annulus 116.

Figure 8:
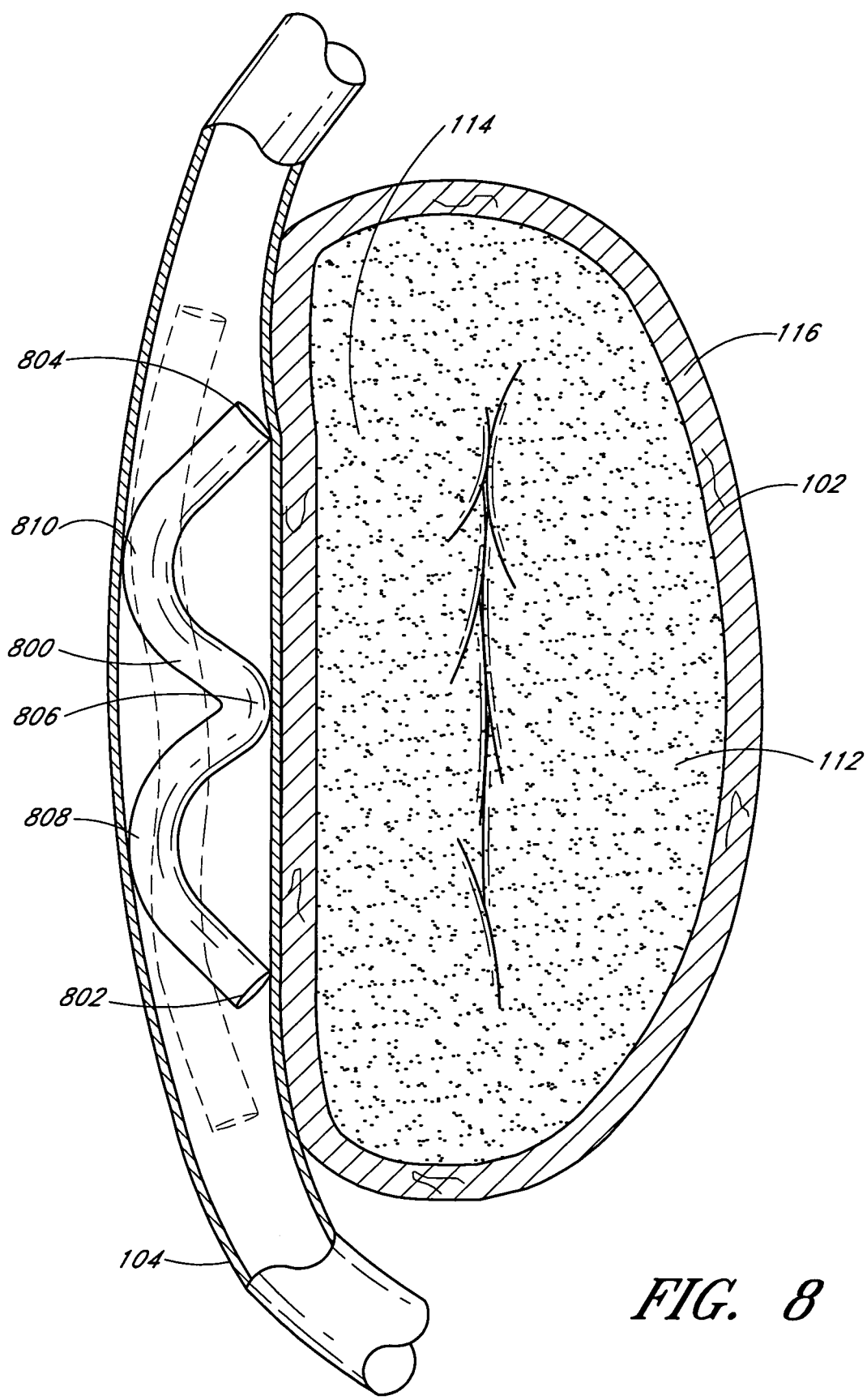
FIG. 8 illustrates a perspective view of a partial section of the heart including a mitral valve and a coronary sinus with yet another exemplifying embodiment of a tissue shaping device positioned therein.

FIG. 8 illustrates another exemplifying embodiment of a tissue shaping device 800 that is dynamically adjustable to effect changes in the shape of the mitral valve annulus 116. In particular, the tissue shaping device 800 is adjustable between at least a first configuration (depicted as dashed lines) and a second configuration (depicted as solid lines). In the first configuration, the tissue shaping device 800 includes a more elongated or extended shape, which advantageously facilitates deployment of the tissue shaping device 800 within the coronary sinus 104. In the second configuration, the tissue shaping device 800 contracts to a wider (e.g., a longer vertical dimension) and less elongated shape.

As shown, the tissue shaping device 800 include a curvilinear shape including ends 802, 804, a center protrusion 806 and side protrusions 808, 810. As the tissue shaping device 800 contracts from the first configuration to the second configuration, the center protrusion 806 extends toward and presses against the coronary sinus wall proximate the mitral valve annulus 116. In particular, the deformation of the tissue shaping device 800 advantageously moves the posterior leaflet 114 of the mitral valve 102 toward the anterior leaflet 112 to facilitate greater coaptation. In yet other embodiments, the tissue shaping device 800 may be situated such that the side protrusions 808, 810 contact the coronary sinus 104 to cause a change in at least one dimension of the mitral valve annulus 116.

Figure 9A:
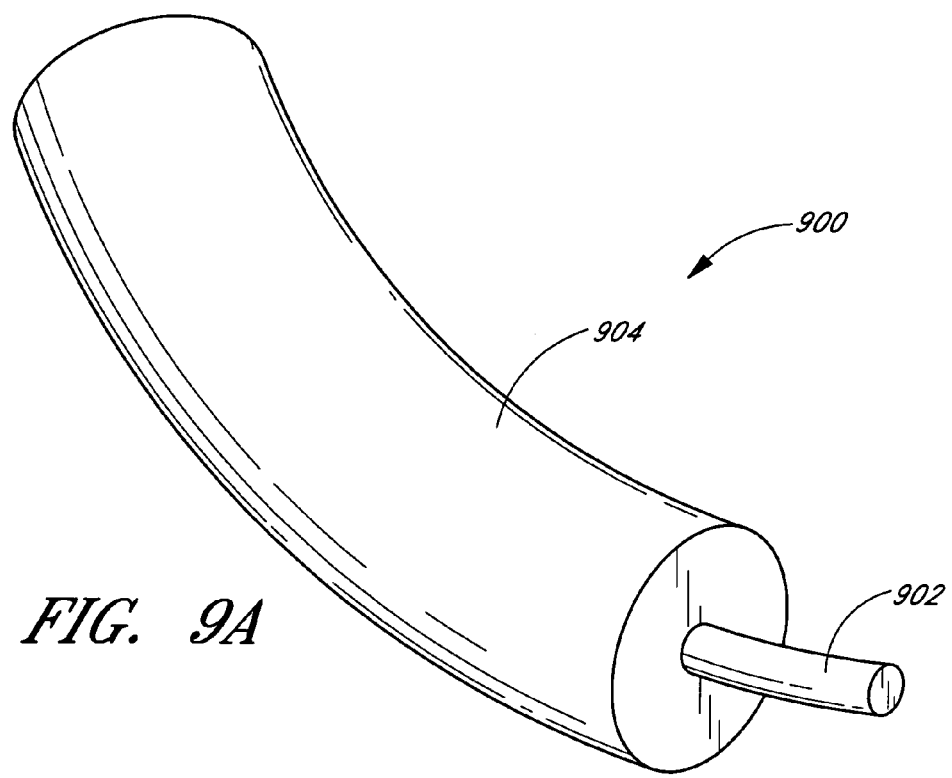
FIG. 9A is a perspective view of a partial section of a tissue shaping device comprising a shape memory wire according to certain embodiments of the invention.

FIG. 9A is an enlarged perspective view of a portion of a tissue shaping device 900, which may be similar to the tissue shaping device 120 shown in FIGS. 1-3B. In particular, the illustrated tissue shaping device 900 includes a wire 902 and a flexible material 904. For illustrative purposes, portions of the flexible material 904 are not shown so as to expose the wire 902.

The term "wire" as use herein is a broad term having its normal and customary meaning and includes, without limitation, mesh, flat, round, band-shaped, and rod-shaped members. In certain embodiments, the wire 902 has a diameter between approximately 0.0254 millimeter and approximately 0.254 millimeter.

In certain embodiments, the wire 902 comprises a shape memory material. Suitable shape memory materials include shape memory polymers or shape memory alloys. For example, in certain embodiments, the wire 902 comprises a NiTi alloy configured to transition to its austenite phase when heated and transform to a memorized shape, as discussed above. In certain such embodiments, the wire 902 is configured to contract to an arcuate shape when transitioning to the austenite phase. In certain such embodiments, the austenite start temperature $A_s$ is in a range between approximately 33° C. and approximately 43° C., the austenite finish temperature $A_f$ is in a range between approximately 45° C. and approximately 55° C., the martensite start temperature $M_s$ is less than approximately 30° C., and the martensite finish temperature $M_f$ is greater than approximately 20° C. In other embodiments, the austenite finish temperature $A_f$ is in a range between approximately 48.75° C. and approximately 51.25° C.

In certain embodiments, the shape memory material of the wire 902 may be cooled to change shape. Certain shape memory alloys, such as NiTi or the like, respond to the application of a temperature below the nominal ambient temperature. After heating of the wire 902 has taken place, the wire 902 is cooled below the $M_s$ temperature to start expanding the tissue shaping device 900. The wire 902 can also be cooled below the $M_f$ temperature to finish the transformation to the martensite phase and reverse the contraction cycle.

As discussed above, certain polymers also exhibit a two-way shape memory effect and can be used in the wire 902 to both expand and contract the tissue shaping device 900 through heating and cooling processes. Cooling can be achieved, for example, by inserting a cool liquid onto or into the tissue shaping device 900 through a catheter, or by cycling a cool liquid or gas through a catheter placed near the tissue shaping device 900. Exemplary temperatures for a NiTi embodiment for cooling and reversing a contraction cycle range between approximately 20° C. and approximately 30° C.

In other embodiments, the wire 902 comprises an energy absorption enhancement material, which includes any material or compound that selectively absorbs and converts a non-invasive heating energy to heat, which is then transferred by thermal conduction to the wire 902. The energy absorption enhancement material allows the tissue shaping device 900 to be actuated and adjusted by the non-invasive application of lower levels of energy and also allows for the use of non-conducting materials, such as shape memory polymers, for the wire 902. In certain embodiments, magnetic flux ranging between approximately 2.5 Tesla and approximately 3.0 Tesla may be used for activation. By allowing the use of lower energy levels, the energy absorption enhancement material also reduces thermal damage to nearby tissue. Suitable energy absorption enhancement materials are discussed in more detail above.

In one embodiment, the energy absorption enhancement material is located within the wire 902 or may be coated on the outside of the wire 902 to enhance energy absorption. It may also be desirable for the energy absorption enhancement material, a carrier material surrounding the energy absorption enhancement material, or both to be thermally conductive. Thus, thermal energy from the energy absorption enhancement material is transferred to the wire 902.

In yet other embodiments, the wire 902 comprises a ferromagnetic shape memory material, as discussed above. In such embodiments, the shape of the wire 902 can be changed by exposing the tissue shaping device 900 and wire 902 to a magnetic field. When using a magnetic field to adjust the tissue shaping device 900, nearby healthy tissue is not exposed to high temperatures that could damage the tissue. Furthermore, since the shape memory material does not need to be heated, the shape and/or size of the tissue shaping device 900 is capable of being adjusted more quickly and more uniformly than by heat activation.

With continued reference to FIG. 9A, the illustrated wire 902 is substantially enclosed in the flexible material 904. In certain embodiments, the flexible material 904 advantageously comprises a biocompatible material, such as for example, silicone rubber. In other embodiments, the flexible material 904 comprises woven polyester cloth, Dacron®, woven velour, polyurethane, polytetrafluoroethylene (PTFE), heparin-coated fabric, combinations of the same or the like. In yet other embodiments, the flexible material 904 comprises a biological material, such as for example, bovine or equine pericardium, homograft, patient graft, or cell-seeded tissue. In certain embodiments, the flexible material 904 is continuous and covers substantially the entire wire 904. In yet other embodiments, the flexible material 904 covers only a portion of the wire 902, such as selected portions of the circumference the wire 902.

In certain embodiments, the flexible material 904 includes a thickness that advantageously allows for the deformation for the wire 902 from a first configuration to second configuration. For example, the flexible material may comprise a thickness of between approximately 0.05 millimeter and approximately 0.762 millimeter.

As discussed above in relation to FIG. 2, in certain embodiments, the progress of the size change of the tissue shaping device 900 can be measured or monitored in real-time conventional imaging techniques. Energy from conventional imaging devices can also be used to activate the shape memory material and change at least one dimension of the tissue shaping device 900.

Furthermore, the tissue shaping device 900 may comprise two or more sections or zones of shape memory material having different temperature response curves. For example, the wire 902 may comprise at least two different shape memory materials.

Figure 9B:
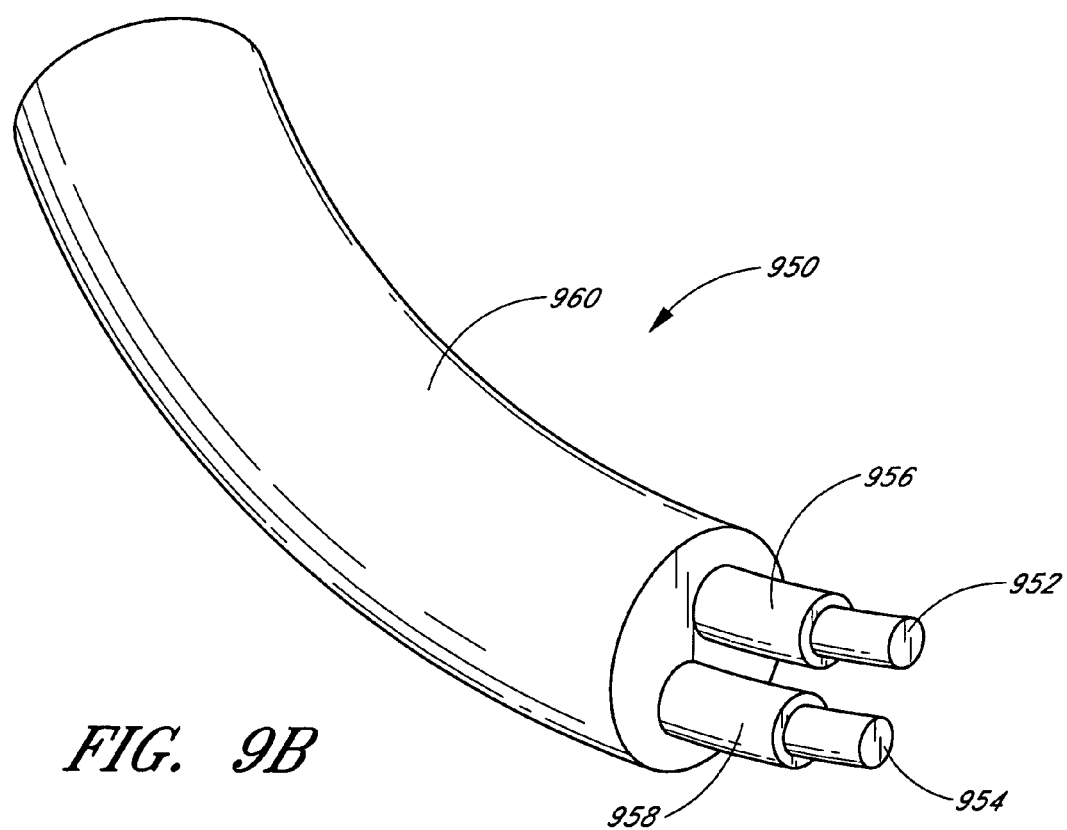
FIG. 9B is a perspective view of a partial section of a tissue shaping device comprising a first wire and a second wire according to certain embodiments of the invention.

FIG. 9B is an enlarged perspective view of a portion of a tissue shaping device 950, which may be similar to the tissue shaping device 120 shown in FIGS. 1-3B. In particular, the illustrated tissue shaping device 950 includes multiple wires therein, including a first wire 952 and a second wire 954. Also illustrated are a first coating 956, a second coating 958 and a flexible material 960, portions of which are shown removed to expose the first wire 952 and the second wire 954.

In certain embodiments, the first wire 952 and second wire 954 advantageously include shape memory materials that have different properties. For example, the first wire 952 may respond to lower temperatures than the second wire 954. Such embodiments advantageously allow the tissue shaping device 950 to be adjusted to multiple configurations. For example, if each of the wires 952, 954 include two shape memory states or configurations, the tissue shaping device 950 is capable of adjusting between four states or configurations.

In certain embodiments, the tissue shaping device 950 is capable of contracting and expanding. For example, as discussed above, after the tissue shaping device 950 has contracted, it may become necessary to expand the tissue shaping device 950. For instance, the tissue shaping device 950 may be implanted in a child with an enlarged heart. When the size of the heart begins to recover to its natural size, and the mitral valve reforms to its generally normal shape, the tissue shaping device 950 can be adjusted. Then, as the child gets older and the heart begins to grow, the tissue shaping device 950 can be further adjusted or removed from the coronary sinus as needed. In such certain embodiments, the first wire 952 may be configured to contract the tissue shaping device 950 and the second wire 954 may be configured to expand the tissue shaping device 950.

With continued reference to FIG. 9B, the outside surface of the first wire 952 is substantially enclosed by the first coating 956, and the outside surface of the second wire 954 is substantially enclosed by the second coating 958. In certain embodiments, the first coating 956 and the second coating 958 each comprise silicone tubing.

In certain other embodiments, the first coating 956 and the second coating 958 each comprise an energy absorption material, such as the energy absorption materials discussed above. In certain embodiments, the first coating 956 heats when exposed to a first form of energy, and the second coating 958 heats when exposed to a second form of energy. For example, the first coating 956 may heat when exposed to MRI energy, and the second coating 958 may heat when exposed to HIFU energy. As another example, the first coating 956 may heat when exposed to RF energy at a first frequency, and the second coating 958 may heat when exposed to RF energy at a second frequency. Thus, the first wire 952 and the second wire 954 can be activated independently such that one transitions to its austenite phase while the other remains in its martensite phase As also shown, the first and second wires 952, 954 and respective coatings 956, 958 are covered by the flexible material 960, which may be similar to the flexible coating 904 depicted in FIG. 9A. In one embodiment, the flexible material 912 operatively couples the first wire 952 and the second wire 954 such that a shape change in one mechanically affects the shape of the other. As discussed above, the first and second wires 952, 954 may each comprise a different shape memory material, such as the shape memory materials discussed above, that are activated at different temperatures.

In certain embodiments, the tissue shaping device 950 is heated to a first temperature that causes the first wire 952 to transition to its austenite phase and contract to its memorized shape. At the first temperature, the second wire 954 is in its martensite phase and is substantially flexible as compared to the contracted first wire 952. Thus, when the first wire 952 transitions to its austenite phase, it exerts a sufficient force on the second wire 954 through the flexible material 960 to deform the second wire 954 and cause the tissue shaping device 950 to change shape.

The tissue shaping device 950 can be expanded by heating the tissue shaping device to a second temperature that causes the second wire 954 to transition to its austenite phase and expand to its memorized shape. In certain embodiments, the second temperature is higher than the first temperature. Thus, at the second temperature, both the first and second wires 952, 954 are in their respective austenite phases.

In one embodiment, the diameter of the second wire 954 is sufficiently larger than the diameter of the first wire 952 such that the second wire 954 exerts a greater force to maintain its memorized shape in the austenite phase than the first wire 952. Thus, the first wire 952 is mechanically deformed by the force of the second wire 954 and the tissue shaping device 950.

In certain embodiments, the first wire 952 is configured to contract when transitioning to its austenite phase. In certain such embodiments, the first wire 952 has an austenite start temperature $A_s$ in a range between approximately 33° C. and approximately 43° C., an austenite finish temperature $A_f$ in a range between approximately 45° C. and approximately 55° C., a martensite start temperature $M_s$ less than approximately 30° C., and a martensite finish temperature $M_f$ greater than approximately 20° C. In other embodiments, the austenite finish temperature $A_f$ of the first wire 952 is in a range between approximately 48.75° C. and approximately 51.25° C.

In certain embodiments, the second wire 954 is configured to expand when transitioning to its austenite phase. In certain such embodiments, the second wire 954 has an austenite start temperature $A_s$ in a range between approximately 60° C. and approximately 70° C., an austenite finish temperature $A_f$ in a range between approximately 65° C. and approximately 75° C., a martensite start temperature $M_s$ less than approximately 30° C., and a martensite finish temperature $M_f$ greater than approximately 20° C. In other embodiments, the austenite finish temperature $A_f$ of the first wire 952 is in a range between approximately 68.75° C. and approximately 71.25° C.

Figure 10A:
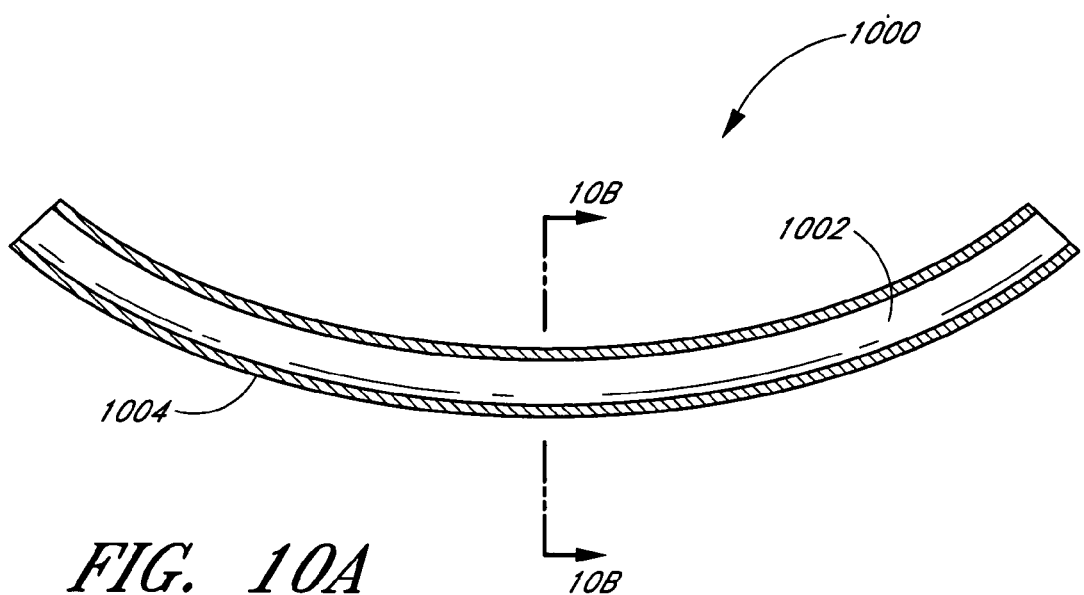
FIG. 10A is a schematic illustration of a side view of a tissue shaping device having an energy-absorbing layer according to certain embodiments of the invention.

FIG. 10A illustrates a tissue shaping device 1000 including a shape memory wire 1002 substantially coated with an energy absorption layer 1004. As discussed above, the energy absorption layer 1004 advantageously enhances energy absorption by other materials, such as the wire 1002. For example, the energy absorption layer 1004 may comprise at least one material and/or structure used to absorb energy from, for example, HIFU, MRI, inductive heating, combinations of the same or the like. In certain embodiments, the energy absorption layer 1004 increases heating efficiency and localizes heating in particular areas of the shape memory wire 1002 such that damage to surrounding tissue is reduced or minimized.

Figure 10B:
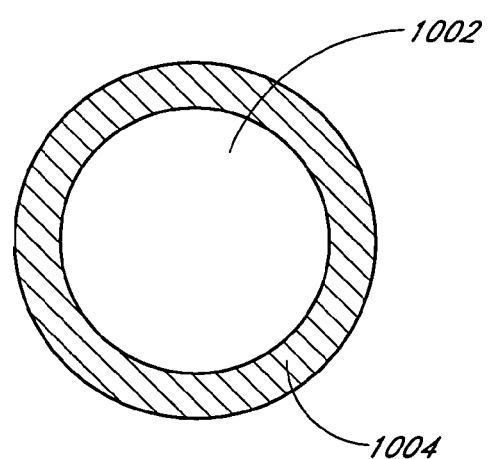
FIG. 10B is a cross-sectional view of the tissue shaping device depicted in FIG. 10A.

FIG. 10B illustrates a cross-sectional view of the tissue shaping device 1000. In particular, the energy absorption layer 1004 is shown as surrounding the outside surface of the shape memory wire 1062. In other embodiments, the energy absorption layer 1004 may comprise multiples layers for improving absorption of energy. For example, different layers may be capable of responding to different types of energy. In certain other embodiments, the energy absorption layer 1004 covers only a portion of the outside surface of the wire 1002, or the energy absorption material may be located within the wire 1002.

Figure 11A:
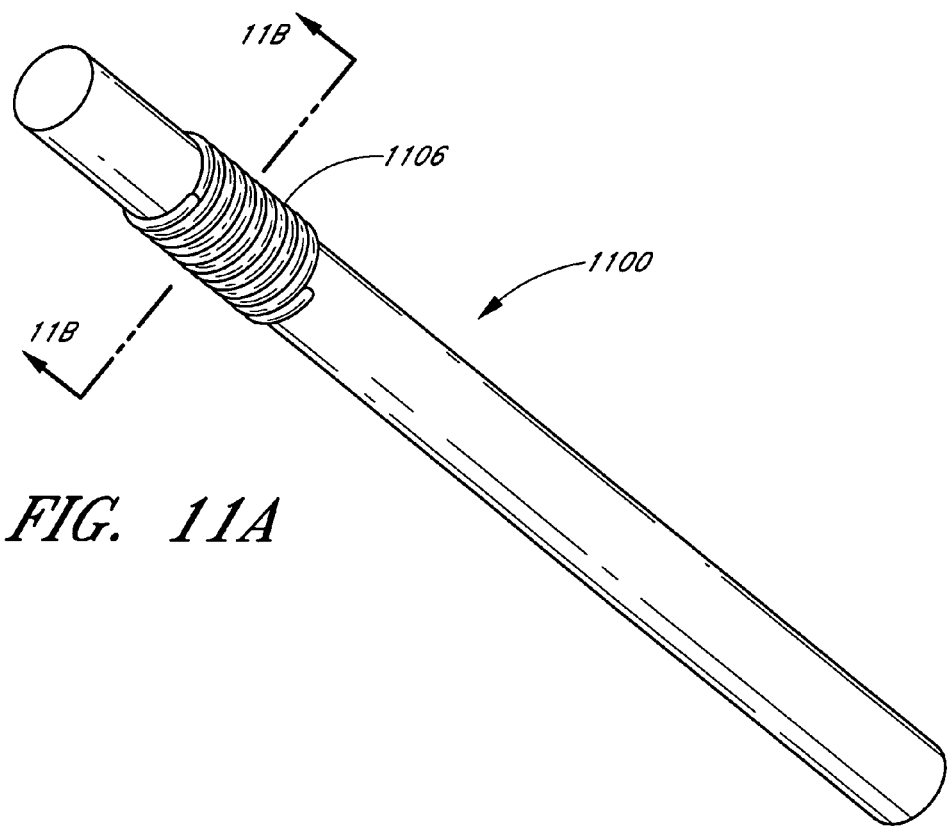
FIG. 11A is a side perspective view of a tissue shaping device further comprising a wire coil according to certain embodiments of the invention.

FIG. 11A illustrates a tissue shaping device 1100 including an electrically conductive coil 1106 according to certain embodiments of the invention. In one embodiment, the tissue shaping device 1100 is similar to the tissue shaping device 1000 of FIGS. 10A and 10B and comprises a shape memory wire responsive to changes in temperature as discussed above.

In one embodiment, the electrically conductive coil 1106 comprises copper, gold, titanium, platinum, platinum iridium, stainless steel, ELGILOY®, alloys or combinations of the same or the like.

Figure 11B:
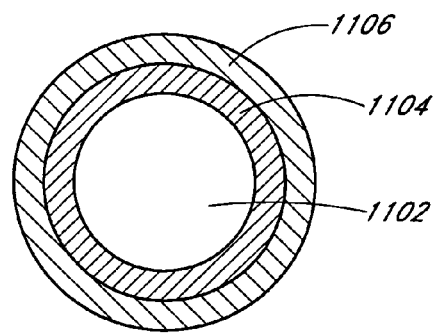
FIG. 11B is a cross-sectional view of the tissue shaping device of FIG. 11A.

FIG. 11B illustrates a cross-sectional view of the tissue shaping device 1100. In particular, illustrated coil 1106 surrounds an energy absorption layer 1104 that covers a shape memory wire 1102, which may be similar to the energy absorption layer 1004 and wire 1002 depicted in FIGS. 10A and 10B.

With reference to FIG. 11A, the illustrated coil 1106 is wrapped around a portion of the wire 1102 where it is desired to focus energy and heat the tissue shaping device 1100. In certain embodiments, the coil 1106 is wrapped around approximately 5% to approximately 15% of the wire 1102. In other embodiments, the coil 1106 is wrapped around approximately 15% to approximately 70% of the wire 1102. In other embodiments, the coil 1106 is wrapped around substantially the entire wire 1102. In further embodiments, the tissue shaping device 1100 may include the energy absorption layer 1104 only between the coil 1106 and the wire 1102 and/or on portions of the wire 1102 not wrapped by the coil 1106. In yet other embodiments, the tissue shaping device 1100 may function without the energy absorption layer 1104.

In certain embodiments, an electric current is non-invasively induced in the coil 1106 using electromagnetic energy. For example, in certain embodiments, a handheld or portable device comprising an electrically conductive coil, which is described in more detail with respect to FIG. 13, generates an electromagnetic field that non-invasively penetrates the patient's body and induces a current in the coil 1106. This electric current, in turn, causes the coil 1106 to heat. The coil 1106, the wire 1102 and the coating 1104 (if any) are advantageously thermally conductive such that heat or thermal energy transfers from the coil 1106 to the wire 1102. Thus, thermal energy can be directed to the wire 1102, or portions thereof, while reducing thermal damage to surrounding tissue.

Figure 11C:
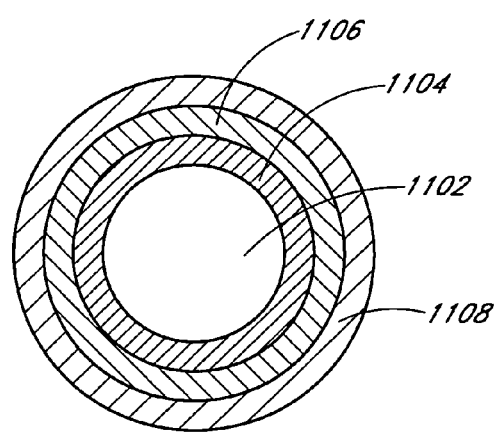
FIG. 11C is a cross-sectional view of the tissue shaping device of FIG. 11A further comprising an outer layer.

FIG. 11C further illustrates the tissue shaping device 1100 as including an outer layer 1108. The outer layer 1108 comprises at least one material for facilitating medical procedures using the tissue shaping device 1100. In certain embodiments, the outer layer 1108 substantially envelops the entire tissue shaping device 1100. In other embodiments, the outer layer 1108 covers only a portion of the tissue shaping device 1100.

In one embodiment, the outer layer 1108 comprises a lubricious material that facilitates placement of the tissue shaping device 1100 within the coronary sinus. In one embodiment, the lubricious material is hydrogel or TEFLON®. In other embodiments, the lubricious material may comprise surface treated silicone or polyurethane materials, combinations of the same or the like.

In another embodiment of the invention, the outer layer 1108 comprises an anti-inflammatory coating to decrease inflammation response by the body of the patient. In one embodiment, the anti-inflammatory coating is Dexamethasone sodium phosphate or Dexamethasone sodium acetate. In other embodiments, the anti-inflammatory coating may comprise heparin or the like.

In certain embodiments, the outer layer 1108 advantageously encapsulates at least a portion of the coil 1106 and/or wire 1102 such that they do not contact tissue or fluid of the patient. For example, the outer layer 1108 may advantageously comprise a biocompatible, flexible material, such as, for example, a polyurethane tube. In other embodiments, the outer layer 1108 may comprise polytetrafluoroethylene ("TEFLON®") or expanded polytetrafluoroethylene (ePTFE). In yet other embodiments, the outer layer 1108 may comprise DACRON®, woven velour, heparin-coated fabric, bovine or equine pericardium, homograft, patient graft, cell-seeded tissue, combinations of the same or the like.

In yet other embodiments, the outer layer 1108 comprises a biodegradable jacket or sleeve that facilities removal of the tissue shaping device 1100 from the coronary sinus. For example, once physical remodeling of the mitral valve has taken place (as determined, for example, by viewing Doppler enhanced echocardiograms), the tissue shaping device 1100 may be removed while the outer layer 1108 remains within the coronary sinus. In one embodiment, the outer layer 1108 advantageously comprises a polylactic acid (PLA). In other embodiments, the outer layer 1108 jacket comprises poly vinyl alcohol (PVA) or the like. In yet other embodiments, the outer layer 1108 comprises multiple layers, such as, for example, a biocompatible inner layer and a biodegradable outer layer.

In addition to the foregoing, embodiments of the tissue shaping devices described herein may include at least one passive fixation mechanism for securing the tissue shaping devices within a vessel, such as the coronary sinus. Such passive fixation mechanisms allow for the tissue shaping device to be temporarily or permanently implanted within the subject vessel and substantially prevent the tissue shaping device from undesired movement within the vessel.

In certain embodiments, the tissue shaping device 700 includes a plurality of fins and/or tines. For example, the fins and/or tines may be connected to, or incorporated in, the outer surface of the tissue shaping device, such as near the ends of the tissue shaping device. In certain embodiments, the fins and/or tines are configured to exert pressure against the wall of the subject vessel such that that tissue shaping device is anchored and is substantially prevented from traveling within the vessel. For instance, the fins and/or tines may advantageously comprise a flexible material, such as, for example, silicone or polyurethane. In other embodiments, the fins and/or tines are advantageously constructed of a braided material, such as, for example, stainless steel, nylon or any other suitable combination of metals and/or polymers.

In yet other embodiments, other types of passive fixation mechanisms may be used. For example, the tissue shaping device may include barbs, bristle-like projections, anchor pads, spikes, helical or round protrusions, combinations of the same or the like. In yet other embodiments of the invention, multiple types of passive fixation mechanisms may be used with the same tissue shaping device. Other types of fixation mechanisms usable with embodiments of the present invention also include active fixation mechanisms, such as, for example, screw-in mechanisms.

In certain embodiments, the tissue shaping devices disclosed herein may also comprise thermal conductors usable to mark desired locations of the tissue shaping device. For example, the thermal conductors may be disposed at locations on the tissue shaping device corresponding to at least one commissure of heart valve leaflets. As another example, the thermal conductors may be used to align a percutaneous energy source, such as a heated balloon inserted through a catheter, with the tissue shaping device. In certain embodiments, the thermal conductors comprise materials such as gold, copper or other like imaging materials.

Figure 12A:
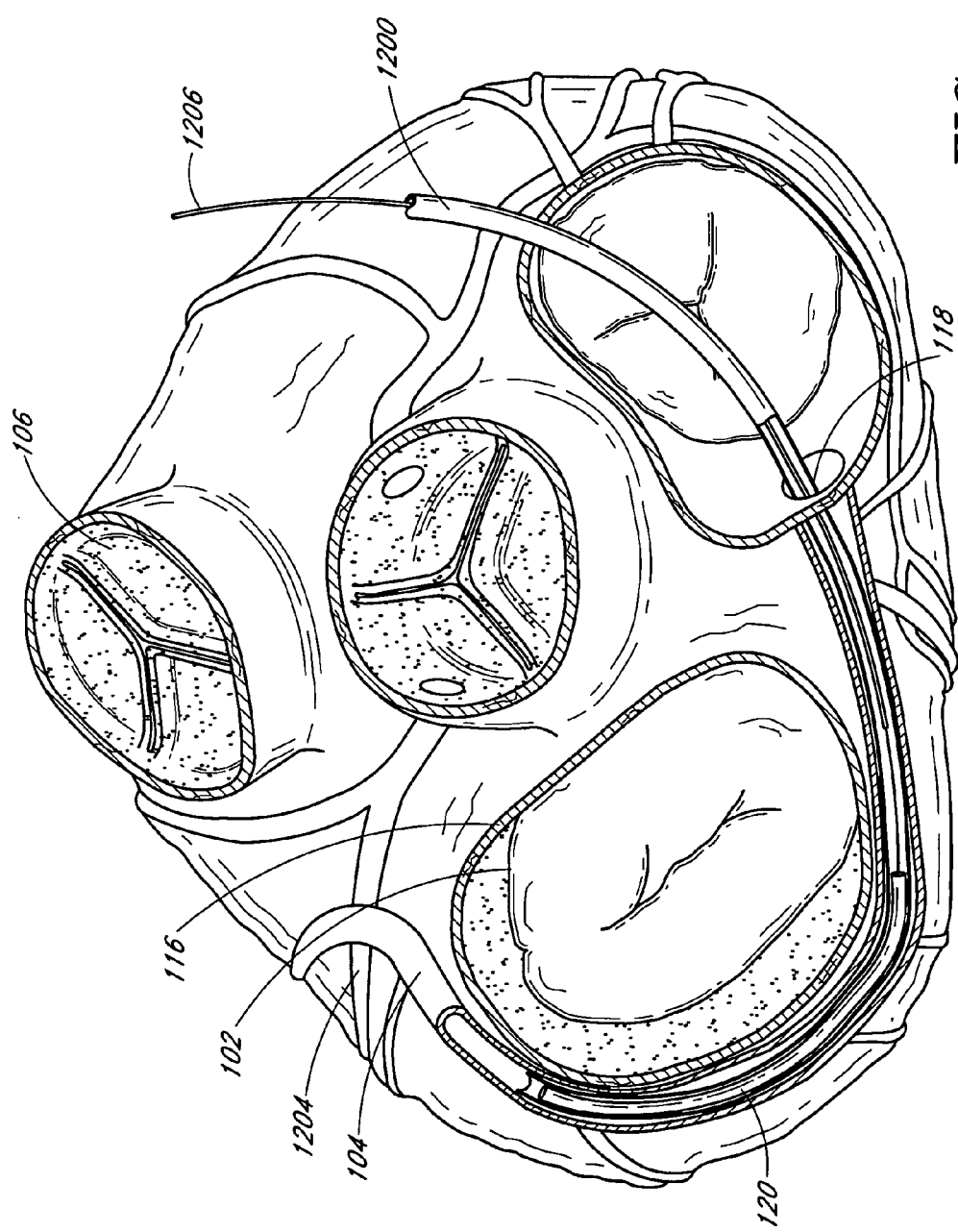
FIGS. 12A-12C illustrate an exemplifying embodiment of a method for positioning a tissue shaping device within a coronary sinus.
Figure 12B:
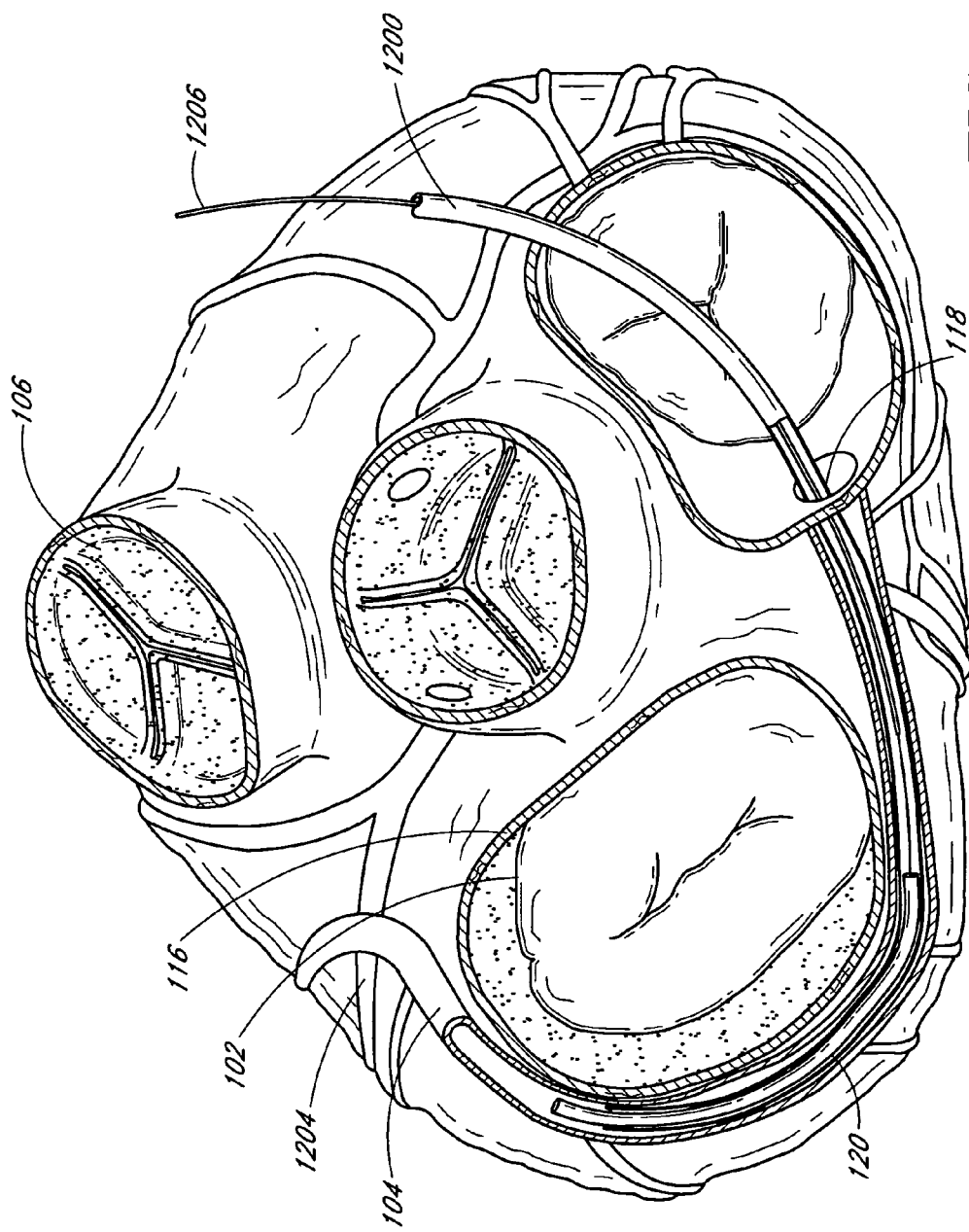
Figure 12C:
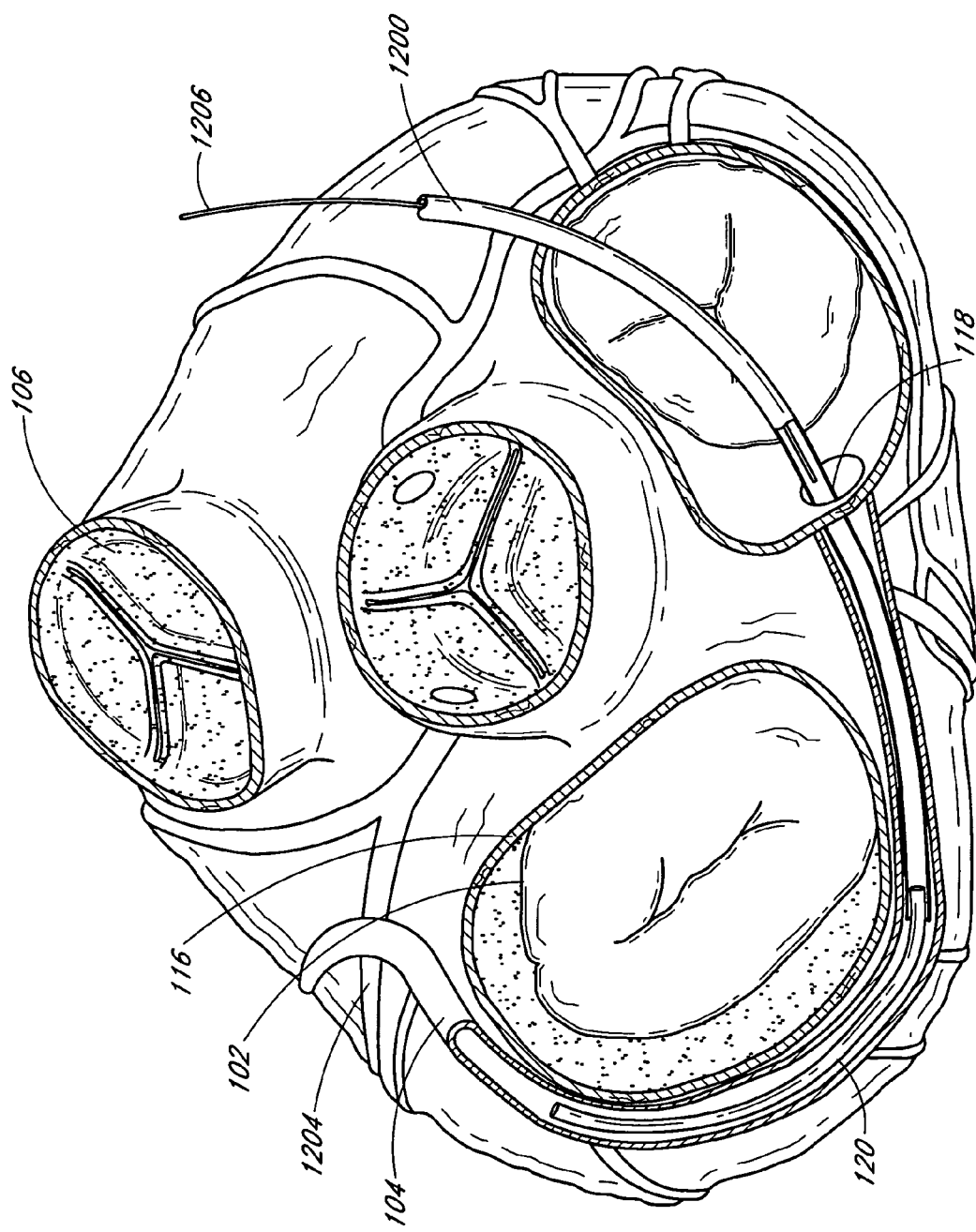

FIGS. 12A-12C depict an exemplary method usable to position the tissue shaping device 120 within the coronary sinus 104. As shown in FIG. 12A, a tubular member, including a catheter 1200, is maneuvered into the coronary sinus 104 through the ostium 118. Disposed within the catheter 1200 is the tissue shaping device 120 in a first configuration, such that deformation of the tissue shaping device 120 has not yet fully occurred.

In one embodiment, the catheter 1200 is used to position the tissue shaping device 120 within the coronary sinus 104 without applying substantial compressive force on the circumflex or other major coronary arteries. For example, the distal end of catheter 1200 may be disposed at a location proximal to the crossover point between the circumflex artery 1204 and the coronary sinus 104, as shown in FIG. 12A. At this point, the catheter 1200 is withdrawn proximally while the tissue shaping device 120 is held stationary, such as by a control wire 1206, to uncover the tissue shaping device 120 within the coronary sinus 104, as is depicted in FIGS. 12B and 12C. Alternatively, the catheter 1200 may be held stationary while the tissue shaping device 120 is advanced out of the distal end of the catheter 1200. In yet other embodiments, other methods known to those skilled in the art may be used to deploy the tissue shaping device 120 within the coronary sinus 104 or other subject vessel or location within the patient's body.

Figure 13:
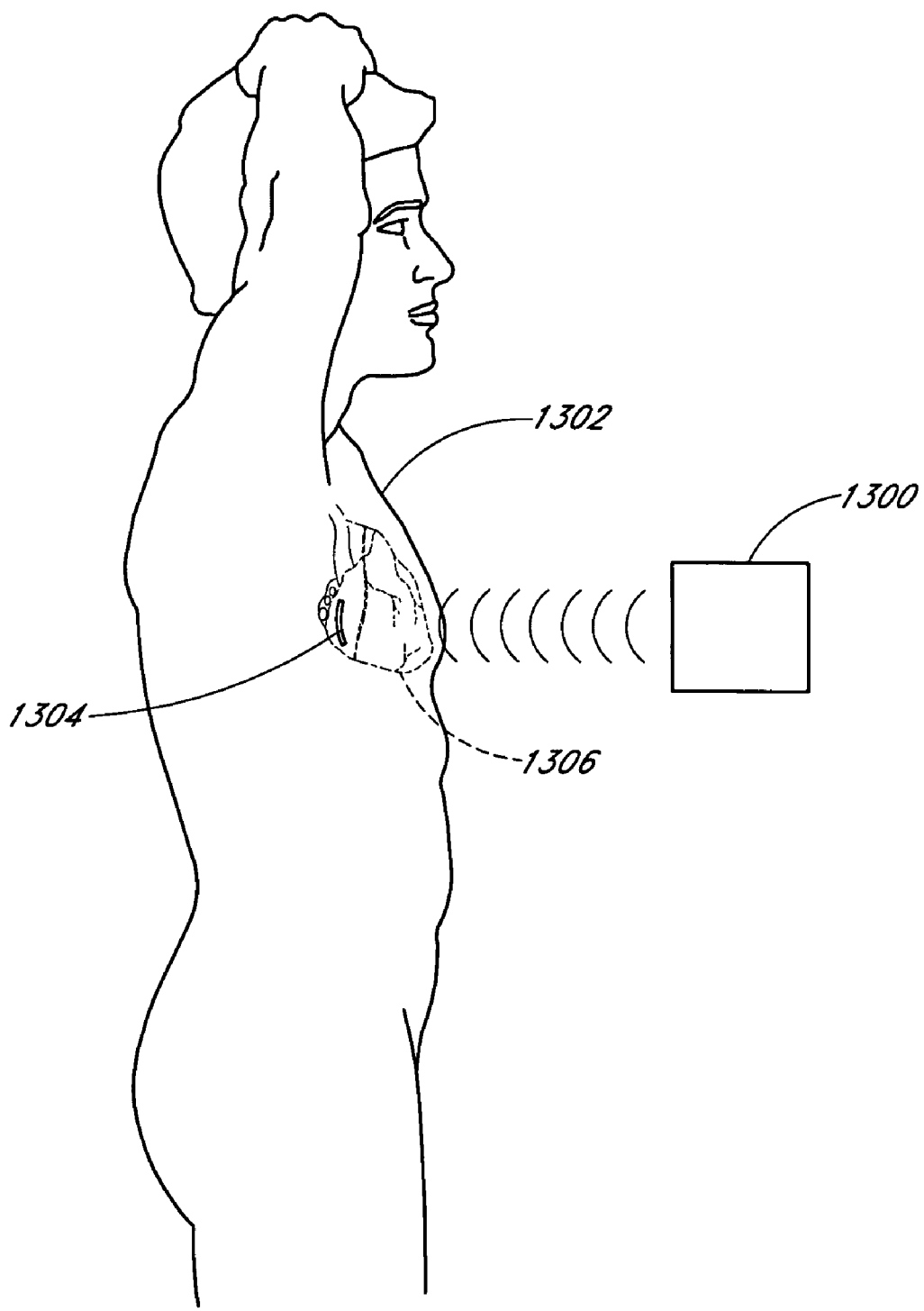
FIG. 13 illustrates a system having an external source for dynamically affecting the shape of a tissue shaping device according to certain embodiments of the invention.

As described previously, in certain embodiments, the tissue shaping device may be advantageously and dynamically adjusted in a non-invasive manner through an energy source located external to the patient's heart. FIG. 13 illustrates a schematic view of an external source 1300 usable outside a patient's body 1302 to adjust a tissue shaping device 1304 positioned within a heart 1306. The external source 1300 includes any transducer, transmitter or the like capable of transmitting energy to the tissue shaping device and usable to effectuate a change in the shape and/or size of the tissue shaping device.

As described previously, the external source 1300 may include an electrically conductive coil for generating an electromagnetic field that non-invasively penetrates the patient's body 1302 and induces a current in the tissue shaping device 1304. In other embodiments, the external source 1300 includes an external HIFU transducer that focuses ultrasound energy onto the tissue shaping device 1304. In yet other embodiments, the external source 1300 is configured to transmit, for example, radio frequency (RF) energy, x-ray energy, microwave energy, acoustic energy, light energy, electric field energy, magnetic field energy, combinations of the foregoing, or the like to the tissue shaping device 1304.

For example, in one embodiment, the tissue shaping device 1304 includes at least one electromagnet. In such an embodiment, the external source 1300 may comprise an electromagnetic transmitter, such as a resistive coil, usable to activate the electromagnet(s) to cause a change in shape of the tissue shaping device 1304. Such a shape change may be used to adjust at least one dimension of the mitral valve annulus. For instance, the tissue shaping device 1304 may include an electromagnet on a first end and a magnetic material on a second end. As the external source 1300 emits a field to activate the electromagnet, the electromagnet attracts or repels the magnetic material, thus causing a change in the shape of the tissue shaping device 1304.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A method of treating mitral valve disease, comprising:
   providing an implant comprising a body having a proximal end, a distal end, and a length extending therebetween, wherein the body comprises at least one shape memory portion consisting essentially of at least one shape memory material, the at least one shape memory portion extending at least half the length of the body;
   positioning the implant in a coronary sinus of the heart; and
   activating the implant with an energy source to cause the at least one shape memory portion to transform from a first configuration to a second configuration while the implant is in the coronary sinus;
   wherein said activating comprises activating with an energy source located outside the coronary sinus and unattached to the implant; and
   wherein said activating comprises activating the at least one shape memory portion with electromagnetic energy emitted from the energy source.

2. The method of claim 1, wherein said activating comprises activating the at least one shape memory portion with radio frequency (RF) energy emitted from the energy source.

3. The method of claim 1, wherein said activating comprises activating the at least one shape memory portion with a magnetic field emitted from the energy source.

4. The method of claim 1, wherein the implant is configured to exert a force on the mitral valve when the shape memory portion is in the second configuration.

5. The method of claim 1, wherein the implant is configured to be deliverable by an elongate delivery device to the coronary sinus through vasculature of the patient when the at least one shape memory portion is in the first configuration.

6. The method of claim 1, wherein the at least one shape memory material comprises a shape memory alloy.

7. The method of claim 1, wherein the at least one shape memory material comprises a shape memory polymer.

8. The method of claim 1, wherein the implant further comprises at least one fixation member configured to substantially anchor the implant within the coronary sinus.

9. The method of claim 1, wherein the body comprises a substantially arcuate shape when the at least one shape memory portion is in the second configuration.

10. The method of claim 1, wherein said activating comprises activating the last least one shape memory portion with focused ultrasound energy emitted from the energy source.

11. The method of claim 1, wherein said activating comprises increasing a temperature of the least one shape memory portion.

12. The method of claim 1, wherein said activating results in little or substantially no tissue damage to tissue proximate the implant.

13. A method of treating mitral valve disease, comprising:
provinding an implant comprising a body having a proximal end, a distal end, and a length extending therebetween, wherein the body comprises at least one shape memory portion consisting essentially of at least one shape memory material, the at least one shape memory portion extending at least half the length of the body;
positioning the implant in a coronary sinus of the heart; and
activating the implant with an energy source to cause the at least one shape memory portion to transform from a first configuration to a second configuration while the implant is in the coronary sinus;
wherein said activating comprises activating the at least one shape memory portion with acoustic energy emitted from the energy source.

14. The implant of claim 13, wherein said activating comprises activating the at least one shape memory portion with focused ultrasound energy emitted from the energy source.

15. The method of claim 13, wherein the implant is configured to exert a force on the mitral valve when the shape memory portion is in the second configuration.

16. The method of claim 13, wherein the implant is configured to be deliverable by an elongate delivery device to the coronary sinus through vasculature of the patient when the at least one shape memory portion is in the first configuration.

17. The method of claim 13, wherein the at least one shape memory material comprises a shape memory alloy.

18. The method of claim 13, wherein the at least one shape memory material comprises a shape memory polymer.

19. The method of claim 13, wherein the implant further comprises at least one fixation member configured to substantially anchor the implant within the coronary sinus.

20. The method of claim 13, wherein the body comprises a substantially arcuate shape when the at least one shape memory portion is in the second configuration.

21. The method of claim 13, wherein said activating comprises increasing a temperature of the least one shape memory portion.

22. The method of claim 13, wherein said activating results in little or substantially no tissue damage to tissue proximate the implant.

* * * * *